US012027237B2

United States Patent
Gross et al.

(10) Patent No.: US 12,027,237 B2
(45) Date of Patent: Jul. 2, 2024

(54) ANOMALOUS FRAGMENT DETECTION AND CLASSIFICATION

(71) Applicant: Grail, LLC, Menlo Park, CA (US)

(72) Inventors: Samuel S. Gross, Sunnyvale, CA (US); Konstantin Davydov, Redwood City, CA (US)

(73) Assignee: GRAIL, LLC, Menlo Park, CA (US)

( * ) Notice: Subject to any disclaimer, the term of this patent is extended or adjusted under 35 U.S.C. 154(b) by 1012 days.

(21) Appl. No.: 16/352,602

(22) Filed: Mar. 13, 2019

(65) Prior Publication Data

US 2019/0287652 A1 Sep. 19, 2019

Related U.S. Application Data

(60) Provisional application No. 62/642,480, filed on Mar. 13, 2018.

(51) Int. Cl.
*G16B 40/00* (2019.01)
*G16B 5/20* (2019.01)
(Continued)

(52) U.S. Cl.
CPC .............. *G16B 40/00* (2019.02); *G16B 5/20* (2019.02); *G16B 20/00* (2019.02); *G16B 30/00* (2019.02);
(Continued)

(58) Field of Classification Search
CPC .......... G16B 40/00; G16B 5/20; G16B 20/00; G16B 30/00; G16H 50/20
(Continued)

(56) References Cited

U.S. PATENT DOCUMENTS

| 8,415,100 B2 | 4/2013 | Markowitz et al. |
| 8,900,829 B2 | 12/2014 | Distler et al. |

(Continued)

FOREIGN PATENT DOCUMENTS

| EP | 1342794 B1 | 12/2005 |
| EP | 1394173 B1 | 10/2007 |

(Continued)

OTHER PUBLICATIONS

Linghao Shen, Jun Zhu, Shuo-Yen Robert Li, Xiaodan Fan, Detect differentially methylated regions using non-homogeneous hidden Markov model for methylation array data, Bioinformatics, vol. 33, Issue 23, Dec. 1, 2017, pp. 3701-3708 (Year: 2017).*

(Continued)

*Primary Examiner* — Russell S Negin
*Assistant Examiner* — Guozhen Liu
(74) *Attorney, Agent, or Firm* — Fenwick & West LLP

(57) ABSTRACT

An analytics system creates a data structure counting strings of methylation vectors from a healthy control group. The analytics system enumerates possibilities of methylation state vectors given a sample fragment from a subject, and calculates probabilities for all possibilities with a Markov chain probability. The analytics system generates a p-value score for the subject's test methylation state vector by summing the calculated probabilities that are less than or equal to the calculated probability of the possibility matching the test methylation state vector. The analytics system determines the test methylation state vector to be anomalously methylated compared to the healthy control group if the p-value score is below a threshold score. With a number of such sample fragments, the analytics system can filter the sample fragments based on each p-value score. The analytics system can run a classification model on the filtered set to predict whether the subject has cancer.

23 Claims, 16 Drawing Sheets

(51) Int. Cl.
*G16B 20/00* (2019.01)
*G16B 30/00* (2019.01)
*G16B 40/20* (2019.01)
*G16H 50/20* (2018.01)
*G16H 50/70* (2018.01)

(52) U.S. Cl.
CPC ............ *G16B 40/20* (2019.02); *G16H 50/20* (2018.01); *G16H 50/70* (2018.01); *C12Q 2600/154* (2013.01)

(58) Field of Classification Search
USPC .......................................................... 702/19
See application file for complete search history.

(56) References Cited

U.S. PATENT DOCUMENTS

| | | |
|---|---|---|
| 9,580,754 B2 | 2/2017 | Markowitz et al. |
| 9,984,201 B2 | 5/2018 | Zhang et al. |
| 10,731,215 B2 | 8/2020 | Ballhause et al. |
| 2005/0221314 A1 | 10/2005 | Berlin et al. |
| 2011/0028333 A1 | 2/2011 | Christensen et al. |
| 2011/0059432 A1 | 3/2011 | Ballhause et al. |
| 2012/0041683 A1 | 2/2012 | Vaske et al. |
| 2013/0079241 A1 | 3/2013 | Luo et al. |
| 2014/0080715 A1 | 3/2014 | Lo et al. |
| 2014/0127688 A1 | 5/2014 | Umbarger et al. |
| 2015/0299809 A1 | 10/2015 | Hansen et al. |
| 2016/0017419 A1 | 1/2016 | Chiu et al. |
| 2016/0017430 A1 | 1/2016 | Badosa |
| 2016/0210403 A1 | 7/2016 | Zhang et al. |
| 2016/0340740 A1 | 11/2016 | Zhang |
| 2016/0340749 A1* | 11/2016 | Stelzer .................. C12N 15/907 |
| 2017/0121767 A1 | 5/2017 | Dor et al. |
| 2017/0175205 A1 | 6/2017 | Toung et al. |
| 2018/0010192 A1 | 1/2018 | Zhang et al. |
| 2018/0143198 A1 | 5/2018 | Wen et al. |
| 2018/0216195 A1 | 8/2018 | Elnitski et al. |
| 2018/0237867 A1 | 8/2018 | Bajic et al. |
| 2018/0327859 A1 | 11/2018 | Van Engeland et al. |
| 2018/0334715 A1 | 11/2018 | Gromminger et al. |
| 2018/0341745 A1 | 11/2018 | Zhang et al. |
| 2019/0032149 A1 | 1/2019 | Van Engeland et al. |
| 2019/0161805 A1 | 5/2019 | Ahlquist et al. |
| 2019/0161806 A1 | 5/2019 | Ahlquist et al. |
| 2019/0256924 A1 | 8/2019 | Vogelstein et al. |
| 2020/0048697 A1 | 2/2020 | Liu |
| 2020/0291459 A1 | 9/2020 | Domanico et al. |

FOREIGN PATENT DOCUMENTS

| | | | |
|---|---|---|---|
| EP | | 1871912 B1 | 2/2012 |
| EP | | 2380993 B1 | 12/2015 |
| EP | | 2670893 B1 | 6/2018 |
| EP | | 3336197 A1 | 6/2018 |
| EP | | 3230476 B1 | 2/2020 |
| EP | | 3390657 B1 | 9/2020 |
| WO | WO 2004/046332 A2 | | 6/2004 |
| WO | WO 2005/019477 A2 | | 3/2005 |
| WO | WO 2006/113770 A2 | | 10/2006 |
| WO | WO 2007/132167 A2 | | 11/2007 |
| WO | WO 2008/084219 A1 | | 7/2008 |
| WO | WO 2011/038507 A1 | | 4/2011 |
| WO | WO 2011/091046 A1 | | 7/2011 |
| WO | WO 2011/092592 A2 | | 8/2011 |
| WO | WO 2011/130751 A1 | | 10/2011 |
| WO | WO 2012/031329 A1 | | 3/2012 |
| WO | WO 2012/071621 A1 | | 6/2012 |
| WO | WO 2012/103031 A2 | | 8/2012 |
| WO | WO 2012/106525 A2 | | 8/2012 |
| WO | WO 2013/066641 A1 | | 5/2013 |
| WO | WO 2013/116375 A1 | | 8/2013 |
| WO | WO 2014/043763 A1 | | 3/2014 |
| WO | WO 2015/116837 A1 | | 8/2015 |
| WO | WO 2015/159292 A2 | | 10/2015 |
| WO | WO 2016/094839 A2 | | 6/2016 |
| WO | WO 2016/101258 A1 | | 6/2016 |
| WO | WO 2016/115530 A1 | | 7/2016 |
| WO | WO 2017/075061 A1 | | 5/2017 |
| WO | WO 2017/106481 A1 | | 6/2017 |
| WO | WO 2017/212428 A1 | | 12/2017 |
| WO | WO 2018/109217 A1 | | 6/2018 |
| WO | WO 2018/119216 A1 | | 6/2018 |
| WO | WO 2018/161031 A1 | | 9/2018 |
| WO | WO 2018/165366 A1 | | 9/2018 |
| WO | WO 2018/195211 A1 | | 10/2018 |
| WO | WO 2018/195217 A1 | | 10/2018 |
| WO | WO 2019/064063 A1 | | 4/2019 |
| WO | WO 2019/067092 A1 | | 4/2019 |
| WO | WO 2019/199696 A1 | | 10/2019 |

OTHER PUBLICATIONS

Douglas D Baumann & RW Doerge (2014) MAGI, Epigenetics, 9:5, 698-703, (Year: 2014).*

Kang, S., Li, Q., Chen, Q et al. CancerLocator: non-invasive cancer diagnosis and tissue-of-origin prediction using methylation profiles of cell-free DNA. Genome Biol 18, 53 (2017). (Year: 2017).*

Felix Krueger, Simon R. Andrews, Bismark: a flexible aligner and methylation caller for Bisulfite-Seq applications, Bioinformatics, vol. 27, Issue 11, Jun. 1, 2011, pp. 1571-1572, (Year: 2011).*

Bibikova, M .et al., "High-throughput DNA methylation profiling using universal bead arrays," Genome Research, vol. 16, Jan. 31, 2006, pp. 383-393.

Broquet, T et al., "Quantifying genotyping errors in noninvasive population genetics," Molecular Ecology, Oct. 2004, pp. 3601-3608.

Chan, K.C.A. et al., "Noninvasive detection of cancer-associated genome-wide hypomethylation and copy number aberrations by plasma DNA bisulfite sequencing," PNAS, vol. 110, No. 47, Nov. 19, 2013 pp. 18761-18768.

Chimonidou, M et al., "SOX17 Promoter Methylation in Circulating Tumor Cells and Matched Cell-Free DNA Isolated from Plasma of Patients with Breast Cancer," Clinical Chemistry 59(1), Jan. 2013, pp. 270-279.

Chu, W-T., "Chapter 12 Solving Linear Equations," An Introduction to Optimization, Spring 2014, pp. 1-47.

Cipriany, B.R. et al., "Single Molecule Epigenetic Analysis in a Nanofluidic Channel," Analytical Chemistry, vol. 82, No. 6, Mar. 15, 2010, pp. 2480-2487.

Coolen, M.W. et al., "Genomic profiling of CpG methylation and allelic specificity using quantitative high-throughput mass spectrometry: critical evaluation and improvements," Nucleic Acids Research, vol. 35, No. 18, e119, Sep. 13, 2007, pp. 1-14.

Da Costa, A.N. et al., "Detection of cancer-specific epigenomic changes in biofluids: Powerful tools in biomarker discovery and application," Molecular Oncology, vol. 6, Iss. 6, Dec. 2012, pp. 704-715.

De Martino, M. et al., "Serum Cell-Free DNA in Renal Cell Carcinoma: A diagnostic and prognostic marker," Cancer, vol. 118, Iss. 1, Jun. 28, 2011, pp. 82-90.

Ehrlich, M., "DNA methylation in cancer: too much, but also too little," Oncogene, vol. 21, Aug. 5, 2002, pp. 5400-5413.

Fackler, M.J. et al., "Quantitative Multiplex Methylation-Specific PCR Assay for the Detection of Promoter Hypermethylation in Multiple Genes in Breast Cancer," Cancer Research, vol. 64, Iss. 13, Jul. 2004, pp. 4442-4452.

Flanagan, J.M. et al., "DNA methylome of familial breast cancer identifies distinct profiles defined by mutation status," The American Journal of Human Genetics, vol. 86, Mar. 12, 2010, pp. 420-433.

Flusberg, B.A et al., "Direct detection of DNA methylation during single-molecule, real-time sequencing," Nature Methods, vol. 7, No. 6, Jun. 2010, pp. 461-467.

Holmes, E.E. et al., "Performance Evaluation of Kits for Bisulfite-Conversion from DNA Tissues, Cell Lines, FFPE Tissues, Aspirates, Lavages, Effusions, Plasma, Serum and Urine," PLoS ONE, vol. 9, Iss. 4, Apr. 3, 2014, pp. 1-15.

(56) References Cited

OTHER PUBLICATIONS

Houseman, E.A. et al., "Reference-free cell mixture adjustments in analysis of DNA methylation data," Bioinformatics, vol. 30, No. 10, Jan. 21, 2014, pp. 1431-1449.
Jin, H. et al., "Chapter 6: Circulating methylated DNA as biomarkers for cancer detection," Methylation—From DNA, RNA and Histones to Diseases and Treatment, Nov. 2012, pp. 137-152.
Kadam, S.K. et al., "Quantitative Measurement of Cell-Free Plasma DNA and Applications for Detecting Tumor Genetic Variation and Promoter Methylation in a Clinical Setting," The Journal of Molecular Diagnostics, vol. 14, No. 4, Jul. 2012, pp. 346-356.
Kit, A.H et al., "DNA Methylation based biomarkers; Practical considerations and applications," Biochimie, vol. 94, Jul. 27, 2012, pp. 2314-2337.
Kuo, H.C et al., "DBCAT: database of CpG island and analytical tools for identifying comprehensive methylation profiles in cancer cells," Journal of Computational Biology, vol. 18, No. 8, Jul. 29, 2011, pp. 1013-1017.
Laird, P.W., "Principles and Challenges of genome-wide DNA methylation analysis," Nature Reviews Genetics, vol. 11, Feb. 2, 2010, pp. 191-203.
Lee, E.J. et al., "Analyzing the cancer methylome through targeted bisulfite sequencing," Cancer Letters, vol. 340, Nov. 2013, pp. 171-178.
Legendre, C. et al., "Whole-genome bisulfite sequencing of cell-free DNA identifies signature associated with metastatic breast cancer," Clinical Epigenetics, vol. 7, Sep. 16, 2015, pp. 1-10.
Li, W. et al., "CancerDetector: ultrasensitive and non-invasive cancer detection at the resolution of individual reads using cell-free DNA methylation sequencing data," Nucleic Acids Research, vol. 46, No. 15, Jun. 12, 2018, pp. 1-11.
Liggett, T.E. et al., "Distinctive DNA methylation patterns of cell-free plasma DNA in women with malignant ovarian tumors," Gynecologic Oncology, vol. 120, Jan. 2011, pp. 113-120.
Lo, Y.M.D. et al., "Genomic Analysis of Fetal Nucleic Acids in Maternal Blood," Annual Review Genomics and Human Genetics, vol. 13, Sep. 2012, pp. 285-306.
Lo, Y.M.D. et al., "Maternal plasma DNA sequencing reveals the genome-wide genetic and mutational profile of the fetus," Science Translational Medicine, vol. 2, Iss. 61, Dec. 8, 2010, pp. 1-13.
Miller, C.A. et al., "ReadDepth: A parallel R package for detecting copy No. alterations from short sequencing reads," PLOS ONE, vol. 6, Iss. 1, Jan. 31, 2011, pp. 1-7.
Ogoshi, K. et al., "Genome-wide profiling of DNA methylation in human cancer cells," Genomics, vol. 98, Iss. 4, Oct. 2011, pp. 280-287.
O'Sullivan, E. et al., "DNA methylation analysis in human cancer," Pancreatic Cancer: Methods and Protocols, Methods in Molecular Biology, vol. 980, Dec. 13, 2012, pp. 131-156.
Page, K. et al., "Detection of HER2 amplification in circulating free DNA in patients with breast cancer," British Journal of Cancer, vol. 104, Mar. 22, 2011, pp. 1342-1348.
Pedersen, I.S. et al., "High recovery of cell-free methylated DNA based on a rapid bisulfite-treatment protocol," BMC Molecular Biology, vol. 13, Mar. 26, 2012, pp. 1-8.
Price, E.M. et al., "Different measures of "genome-wide" DNA methylation exhibit unique properties in placental and somatic tissues," Epigenetics, vol. 7, Iss. 6, Jun. 2012, pp. 652-663.
Quackenbush, J., "Microarray data normalization and transformation," Nature Genetics Supplement, vol. 32, Dec. 2002, pp. 496-501.
Radpour, R. et al., "Hypermethylation of tumor suppressor genes involved in ciritical regulatory pathways for developing a blood-based test in breast cancer," PLOS One, vol. 6, Iss. 1, Jan. 24, 2011, pp. 1-11.
Robinson, M.D. et al. "Evaluation of affinity-based genome-wide DNA methylation data: Effects of CpG density, amplification bias, and copy number variation," Genome Research, vol. 20, Nov. 2, 2010, pp. 1718-1729.
Saied, M.H. et al., "Genome wide analysis of acute myeloid leukemia reveal leukemia specific methylome and subtype specific hypomethylation of repeats," PloS ONE, vol. 7, No. 3, Mar. 29, 2012, pp. 1-12.
Schwarzenbach, H. et al., "Cell-free nucleic acids as biomarkers in cancer patients," Nature Reviews Cancer, May 12, 2011, pp. 1-12.
Shaw, J.A. et al., "Genomic analysis of circulating cell free DNA infers breast cancer dormancy," Genome Research, vol. 22, Oct. 11, 2011, pp. 220-231.
Tanic, M. et al., "Epigenome-wide association studies for cancer biomarker discovery in circulating cell-free DNA: technical advances and challenges," Current Opinion in Genetics & Development, vol. 42, Feb. 2017, pp. 48-55.
Van De Voorde, L. et al., "DNA methylation-based biomarkers in serum of patients with breast cancer," Mutation Research, vol. 751, Jun. 12, 2012, pp. 304-325.
Weisenberger, D.J. et al., "DNA methylation analysis by digital bisulfite genomic sequencing and digital MethyLight," Nucleic Acids Research, vol. 36, No. 14, Jul. 15, 2008, pp. 4689-4698.
Wu, G. et al., "Statistical Quantification of Methylation Levels by Next-Generation Sequencing," PLoS ONE, vol. 6, Iss. 6, Jun. 15, 2011, pp. 1-12.
Yu, M. et al., "Tet-assisted bisulfite sequencing of 5-hydroxyethylcyctosine," Nature Protocols, vol. 7, No. 12, Nov. 29, 2012, pp. 2159-2170.
Yuen, R.K.C. et al., "Genome-wide mapping of imprinted differentially methylated regions of DNA methylation profiling of human placentas from triploidies," Epigenetics & Chromatin, vol. 4, Article No. 10, Jul. 13, 2011, pp. 1-16.
Zhai, R. et al., "Genome-wide DNA Methylation Profiling of Cell-Free Serum DNA in Esophageal Adenocarcinoma and Barrett Esophagus," Neoplasia 14(1), Jan. 2012, pp. 29-33.
Guo, S. et al., "Identification of methylation haplotype blocks aids in deconvolution of heterogeneous tissue samples and tumor tissue-of-origin mapping from plasma DNA," Nature Genetics, vol. 49, No. 4, Apr. 2017, pp. 635-644.
Xu, R. et al., "Circulating tumour DNA methylation markers for diagnosis and prognosis of hepatocellular carcinoma," Nature Materials, Oct. 9, 2017, pp. 1-8.
PCT Invitation to Pay, PCT Application No. PCT/US2019/022122, Jul. 1, 2019, 23 pages.
Kang, S. et al., "CancerLocator: non-invasive cancer diagnosis and tissue-of-origin prediction using methylation profiles of cell-free DNA," Genome Biology, vol. 18, No. 53, 2017, pp. 1191-1195.
PCT International Search Report and Opinion, PCT Application No. PCT/US2019/068060, Apr. 17, 2020, 19 pages.
PCT International Search Report and Opinion, PCT Application No. PCT/US2019/068014, Apr. 17, 2020, 17 pages.
Shen, S. Y. et al., "Sensitive tumour detection and classification using plasma cell-free DNA methylomes," Nature, vol. 563, Nov. 22, 2018, pp. 579-583.
PCT International Search Report and Written Opinion, PCT Application No. PCT/US2019/022122, Aug. 23, 2019, 25 pages.
Grail, Inc., "The Circulating Cell-free Genome Atlas Study (CCGA)," ClinicalTrials.gov Identifier: C1 NCT02889978, Feb. 11, 2019, six pages, [Online] [Retrieved on Apr. 3, 2020] Retrieved from the Internet <URL: https://www.clinicaltrials.gov/ct2/show/NCT02889978>.
"IHEC—International Human Epigenome Consortium,", Date Unknown, four pages, [Online] [Retrieved on Apr. 3, 2021] Retrieved from the Internet <URL:https://ihec-epigenomes.org/>.
Milani, L. et al., "DNA methylation for subtype classification and prediction of treatment outcome in patients with childhood acute lymphoblastic leukemia," Blood, vol. 115, No. 6, Feb. 11, 2010, pp. 1214-1225.
Angermueller, C. et al., "DeepCpG: accurate prediction of single-cell DNA methylation states using deep learning." Genome biology 18 (1) Apr. 11, 2017, pp. 1-13.
Khwaja, M. et al., "A deep autoencoder system for differentiation of cancer types based on DNA methylation state," arXiv:1810.01243v2, Oct. 5, 2018, pp. 1-8.
Margolin, G. et al., "Robust Detection of DNA Hypermethylation of ZNF154 as a Pan-Cancer Locus with in Silico Modeling for

(56) References Cited

OTHER PUBLICATIONS

Blood-Based Diagnostic Development," The Journal of Molecular Diagnostics, vol. 18, Issue 2, Mar. 2016, pp. 283-298.
Taiwan Intellectual Property Office, Office Action, TW Patent Application No. 108108527, Mar. 6, 2023, 10 pages.
United States Office Action, U.S. Appl. No. 16/723,411, filed Apr. 13, 2023, 42 pages.
United States Office Action, U.S. Appl. No. 16/723,716, filed Dec. 21, 2022, 13 pages.
Wu et al., "Redefining CpG islands using hidden Markov models," Biostatistics, 2010, 11(3), pp. 499-514.
Yassi, M. et al., "DMRFusion: a differentially methylated region detection tool based on the ranked fusion method," Genomics, vol. 110, Issue 6, Nov. 1, 2018, pp. 366-374.

\* cited by examiner

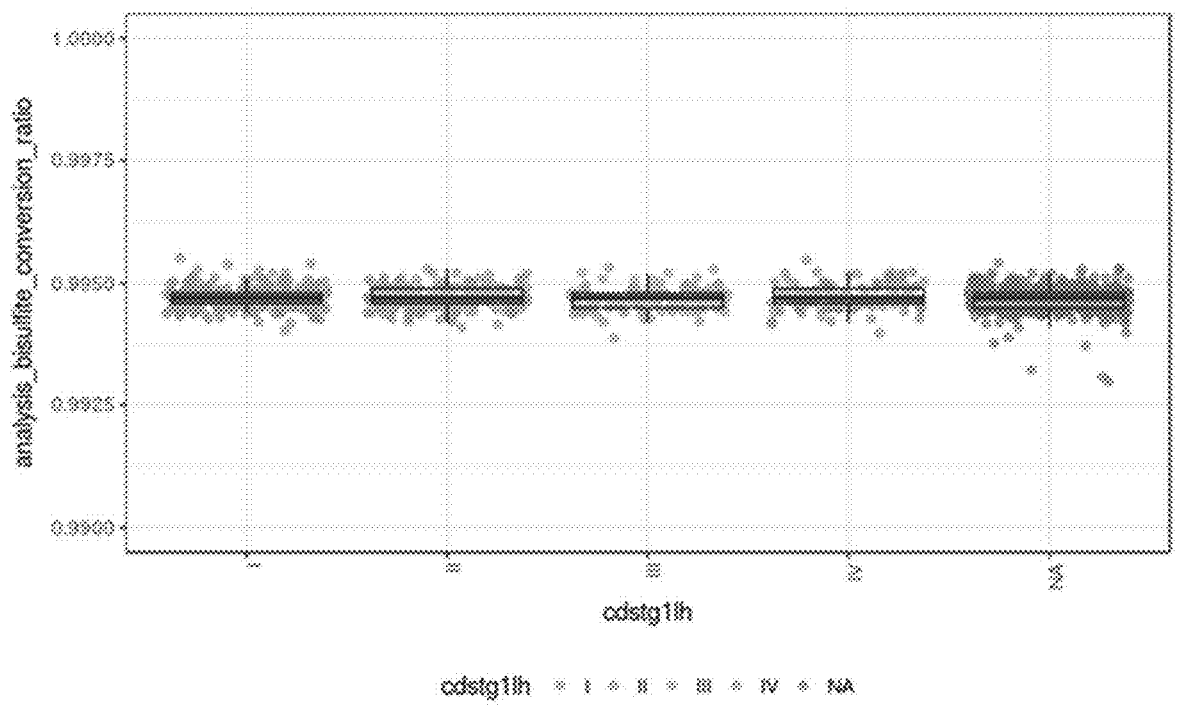
Conversion Accuracy
170
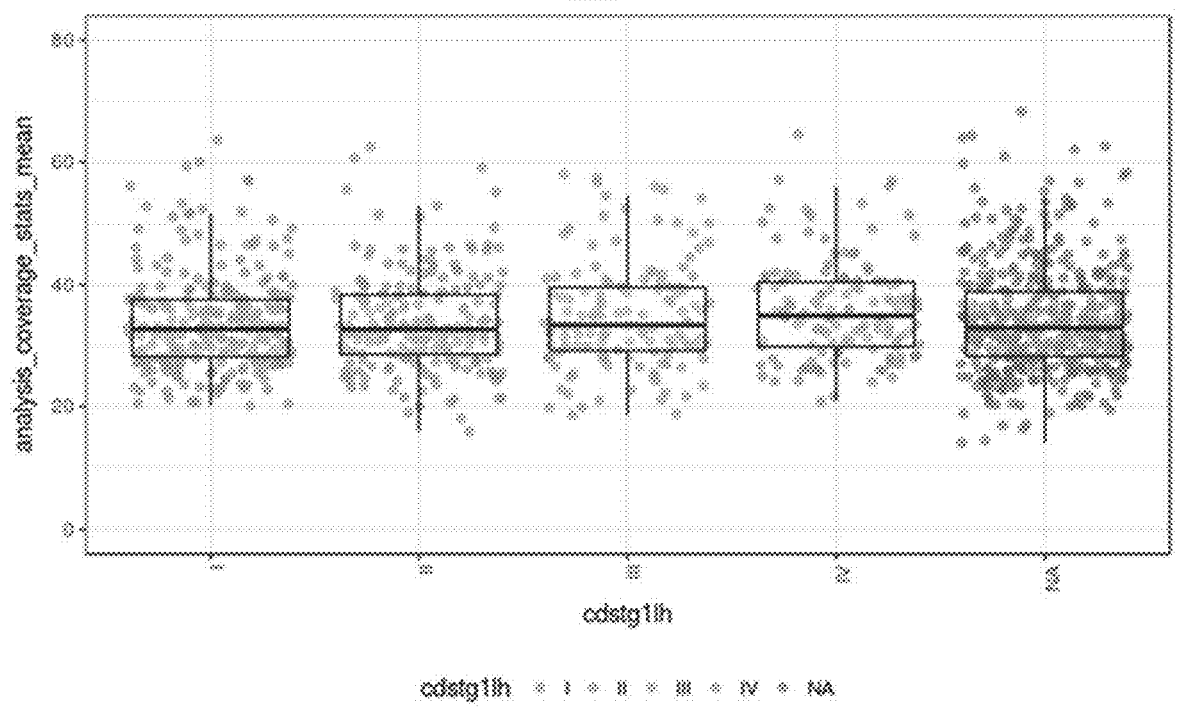
Consistent Fragment Length
180
FIG. 1C

Generate data structure for a control group
200

Generate set of methylation state vectors
for a control group
100

For each methylation state vector, subdivide into
strings of methylation sites
210

Tally strings for each position and methylation
state combination
220

Create data structure storing counts of all
possible strings from the control group
230

Validate data structure consistency
240

FIG. 2

Calculate P-Value with
Markov Chain Model
500

Test Methylation State Vector
505

$< M_{23}, M_{24}, M_{25}, U_{26} >$

| | |
|---|---|
| 410 | |
| 420 | |

| P | $< M_{23}, M_{24}, M_{25}, M_{26} >$ |
|---|---|
| P | $< M_{23}, M_{24}, M_{25}, U_{26} >$ |
| ⋮ | ⋮ |
| P | $< U_{23}, U_{24}, U_{25}, U_{26} >$ |

$= P(M_{26} | M_{23}, M_{24}, M_{25}) * P(M_{25} | M_{23}, M_{24}) * P(M_{24} | M_{23}) * P(M_{23})$
$\approx P(M_{26} | M_{24}, M_{25}) * P(M_{25} | M_{23}, M_{24}) * P(M_{24} | M_{23}) * P(M_{23})$ $= P(U_{26} | U_{23}, U_{24}, U_{25}) * P(U_{25} | U_{23}, U_{24}) * P(U_{24} | U_{23}) * P(U_{23})$
$\approx P(U_{26} | U_{24}, U_{25}) * P(U_{25} | U_{23}, U_{24}) * P(U_{24} | U_{23}) * P(U_{23})$ Probabilities of Possible
Methylation State Vectors
515

430

| p-value | $< M_{23}, M_{24}, M_{25}, U_{26} >$ |
|---|---|

$= \sum [\textit{All probabilities} \leq P(<M_{23}, M_{24}, M_{25}, U_{26}>)]$

P-Value of Test Methylation
State Vector
525

FIG. 5

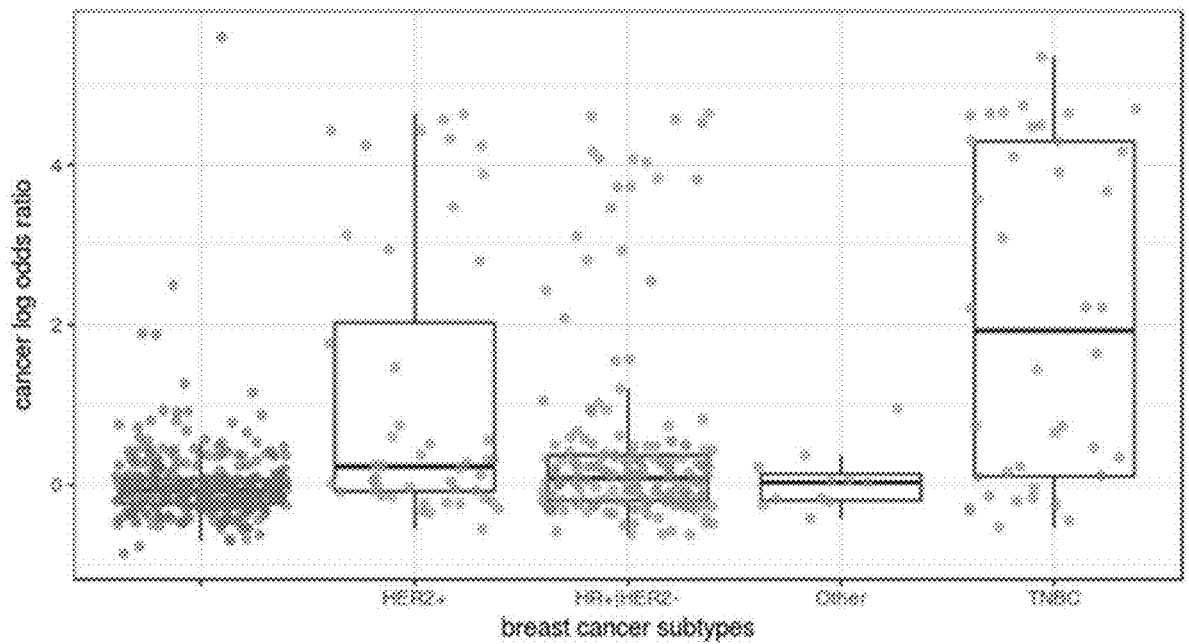
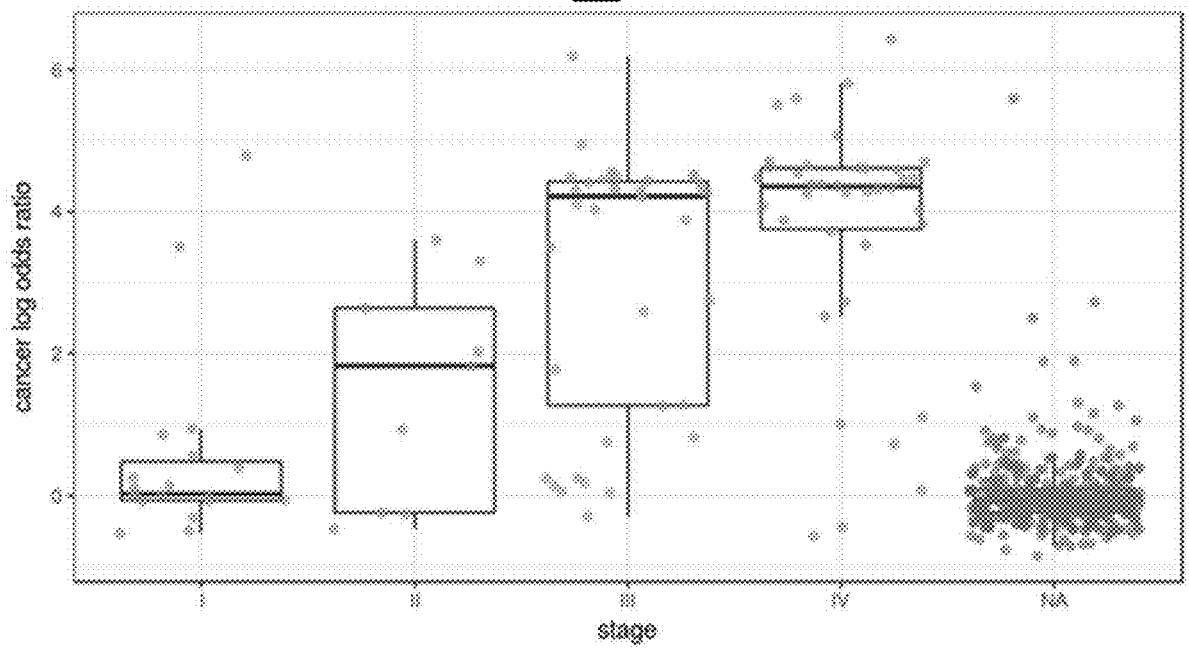
FIG. 7B

ANOMALOUS FRAGMENT DETECTION AND CLASSIFICATION

CROSS REFERENCE TO RELATED APPLICATION

This application claims the benefit of and priority to U.S. Provisional Application No. 62/642,480, filed on Mar. 13, 2018, which is incorporated herein by reference in its entirety for all purposes.

BACKGROUND

Field of Art

DNA methylation plays an important role in regulating gene expression. Aberrant DNA methylation has been implicated in many disease processes, including cancer. DNA methylation profiling using methylation sequencing (e.g., whole genome bisulfite sequencing (WGBS)) is increasingly recognized as a valuable diagnostic tool for detection, diagnosis, and/or monitoring of cancer. For example, specific patterns of differentially methylated regions and/or allele specific methylation patterns may be useful as molecular markers for non-invasive diagnostics using circulating cell-free DNA. However, there remains a need in the art for improved methods for analyzing methylation sequencing data from cell-free DNA for the detection, diagnosis, and/or monitoring of diseases, such as cancer.

SUMMARY

Early detection of cancer in subjects is important as it allows for earlier treatment and therefore a greater chance for survival. Sequencing of cell-free DNA (cfDNA) fragments and analysis of methylation states of various dinucleotides of cytosine and guanine (known as CpG sites) in the fragments provide insight into whether a subject has cancer. Towards that end, this description includes methods for analyzing methylation states of CpG sites of cfDNA fragments. Specifically, the present disclosure provides a method of identifying a cfDNA fragment having or likely to have an anomalous methylation pattern. Fragments occurring at high frequency in individuals without cancer are unlikely to produce highly discriminatory features for classification of cancer status. Thus, identification of cfDNA fragments having an anomalous methylation pattern relative to cfDNA fragments from a healthy sample (e.g., a subject without cancer) are important for selection of cfDNA fragments that may be indicative for detecting cancer-specific methylation patterns with low noise. Among the low noise regions, cfDNA fragments derived from genomic regions most informative in discriminating a cancer patient and a healthy subject, or subjects having other health conditions can be selected. The discrimination between a cancer patient and a healthy subject can be performed with a classifier trained on methylation sequencing data obtained from subjects with cancer, and/or methylation sequencing data from subjects without cancer. Further provided is validation data demonstrating that analysis of anomalously methylated cfDNA fragments identified using the method described herein can be used to detect cancer with high sensitivity and specificity.

In one embodiment, a test sample including a plurality of cfDNA fragments is obtained from a subject of a control group. The plurality of cfDNA fragments in the test sample are treated to convert unmethylated cytosines to uracils, the cfDNA fragments sequenced and compared to a reference genome to identify the methylation state for each of a number CpG sites. An analytics system creates a data structure counting, for each identified CpG site in the reference genome, the number of fragments from the control group having a particular methylation string of some number of CpG sites being methylated vs. unmethylated, starting at that CpG site.

The analytics system creates a methylation state vector for each sequenced fragment where the methylation state vector comprises the CpG sites in the fragments as well as their methylation state—e.g., methylated, unmethylated or indeterminate. For each of the fragments, the analytics system uses probabilistic analysis and the control group data structure to identify the unexpectedness of observing a given fragment (or portion thereof) having the observed methylation states at the CpG sites in the fragment. In one specific embodiment, this probabilistic analysis enumerates the alternate possibilities of methylation state vectors having a same length (in sites) and position within the reference genome as a given fragment (or portion thereof), and uses the counts from the data structure to determine the probability for each such possibility. The analytics system may use a Markov chain probability analysis (along with a given a maximum order for the Markov chain) to model the probability of each such methylation state vector possibility. After calculating probabilities for each possibility of methylation state vector, the analytics system generates a p-value score for the fragment by summing those probabilities for possibilities of methylation state vectors smaller than the probability for the possibility matching the test methylation state vector. The analytics system compares the generated p-value against a threshold to identify cfDNA fragments that are anomalously methylated (also referred to herein as fragments having anomalous methylation patterns) relative to the control group.

In addition to the analytics system described above, a classifier helps to classify a subject as having cancer or not having cancer based on a probability. The classifier is trained on methylation sequencing data obtained from subjects with cancer, and/or methylation sequencing data from subjects without cancer. After sequencing and generating a methylation state vector for each sequenced cfDNA fragment, the classifier is trained using cfDNA fragments identified as being hypomethylated or hypermethylated compared to healthy controls. As used herein "hypomethylated" cfDNA fragments can be defined as fragments having at least 5 CpG sites with at least 80% of the CpG sites being unmethylated. Similarly, "hypermethylated" cfDNA fragments can be defined as fragments having at least 5 CpG sites with at least 80% of the CpG sites being methylated. Next, the classifier runs through each and every CpG site in the genome and calculates a hypomethylation score and a hypermethylation score. Both scores are calculated similarly. For the hypomethylation score, the classifier calculates a ratio of cancer fragments deemed hypomethylated containing the current CpG site over all fragments, cancer and non-cancer, deemed hypomethylated containing the current CpG site. The hypermethylation score for each CpG site is calculated similarly taking a ratio of cancer fragments deemed hypermethylated over all fragments deemed hypermethylated.

Now the classifier takes a subject from the training groups along with their plurality of cfDNA fragments and sequences the fragments to generate methylation state vectors. With each methylation state vector for that subject, the classifier calculates an aggregate hypermethylation score and an aggregate hypomethylation score. Each of the aggregate scores being calculated based off of the hypomethylation scores and hypermethylation scores of the various CpG sites. Then the classifier ranks the subject's methylation state vectors by their aggregate hypomethylation score and also ranks by their aggregate hypermethylation score. With the two rankings, the classifier generates a feature vector for that subject by selecting scores from the ranking. The classifier is then trained to distinguish feature vectors corresponding to the non-cancer training group from feature vectors corresponding to the cancer training group. In one embodiment, the classifier utilizes a L2-regularized kernel logistic regression with a Gaussian radial basis function kernel (RBF kernel).

Accordingly, in one aspect, the present disclosure provides a method for detecting an anomalous methylation pattern in a cell-free deoxyribonucleic acid (cfDNA) sample fragment, the method comprising: accessing a data structure comprising counts of strings of CpG sites within a reference genome and their respective methylation states from a set of training fragments; generating a sample state vector for a sample fragment comprising a sample genomic location within the reference genome and a methylation state for each of a plurality of CpG sites in the sample fragment, each methylation state determined to be methylated or unmethylated; enumerating a plurality of possibilities of methylation states from the sample genomic location that are of a same length as the sample state vector; for each of the possibilities, calculating a probability by accessing the counts stored in the data structure; identifying the possibility that matches the sample state vector and correspondingly the calculated probability as a sample probability; based on the sample probability, generating a score for the sample fragment of the sample state vector relative to the set of training fragments; and determining whether or not the sample fragment has an anomalous methylation pattern based on the generated score.

In some embodiments, each of the strings of CpG sites comprises the methylation state for each of the CpG sites at a plurality of genomic locations within the reference genome, wherein each of the methylation states is determined to be methylated or unmethylated.

In some embodiments, the method further comprises: building the data structure from the set of training fragments and comprising: for each training fragment in the set of training fragments, generating a training state vector comprising a known genomic location within the reference genome and the methylation state for each of the plurality of CpG sites in the training fragment, each methylation state determined to be methylated or unmethylated; determining a plurality of strings, wherein each string is a portion of the training state vector, quantifying a count of each string from the training state vectors; and storing a plurality of counts for each string in the data structure.

In some embodiments, the step of determining whether the sample fragment has an anomalous methylation pattern based on the generated score further comprises determining whether the generated score for the sample fragment is below a threshold score, wherein the threshold score indicates a degree of confidence that the sample fragment has an anomalous methylation pattern. In some embodiments, the threshold score is 0.1 or smaller.

In some embodiments, the set of training fragments comprise training fragments from one or more healthy subjects, wherein the one or more healthy subjects lack a specific medical disorder and wherein the sample fragment is determined to be anomalously methylated relative to the set of training fragments from the one or more healthy subjects.

In some embodiments, generating the score for the sample fragment comprises: identifying calculated probabilities for possibilities of methylation states that are less than the sample probability; and generating the score for the sample fragment by summing all the identified probabilities with the sample probability. In some embodiments, the step of calculating a probability by accessing the counts stored in the data structure for each of the possibilities comprises: for each of a plurality of conditional elements, wherein each conditional element is a conditional probability considering a subset of CpG sites in the possibility, calculating a Markov chain probability of an order with the plurality of counts stored in the data structure by the steps comprising: identifying a first count of number of strings matching that conditional element; identifying a second count of number of strings matching that conditional element's prior methylation states up to the whole number length; and calculating the Markov chain probability by dividing the first count by the second count. In some embodiments, the order is selected from the group consisting of: 1, 2, 3, 4, 5, 6, 7, 8, 9, 10, 11, 12, 13, 14, and 15. In some embodiments, the step of calculating a Markov chain probability of an order with the plurality of counts stored in the data structure further comprises implementing a smoothing algorithm.

In some embodiments, the sample state vector is partitioned into a plurality of windows comprising a first window and a second window, wherein the first window and the second window are two different portions of the sample fragment; wherein identifying the possibility that matches the sample state vector and correspondingly the calculated probability as the sample probability comprises identifying a first possibility with a first sample probability that matches the first window and a second possibility with a second sample probability that matches the second window; and wherein the generated score is based on one of the first sample probability and the second sample probability.

In some embodiments, the method further comprises filtering a plurality of sample fragments based on the generated scores for each sample fragment, resulting in a subset of sample fragments having anomalous methylation patterns.

In some embodiments, the method further comprises identifying the sample fragment as hypermethylated when the sample fragment comprises at least a threshold number of CpG sites with more than a threshold percentage of the CpG sites being methylated. In some embodiments, the threshold number of CpG sites is 5 or more CpG sites, and wherein the threshold percentage of CpG sites methylated is 80% or greater. In some embodiments, the method further comprises identifying the sample fragment as hypomethylated when the sample fragment comprises at least a threshold number of CpG sites with more than a threshold percentage of the CpG sites being unmethylated. In some embodiments, the threshold number of CpG sites is 5 or more CpG sites, and wherein the threshold percentage of CpG sites unmethylated is 80% or greater.

In some embodiments, the method further comprises: applying the sample state vector to a classifier, trained with a cancer set of training fragments from one or more subjects with cancer and a non-cancer set of training fragments from one or more subjects without cancer, wherein the classifier can be used to determine whether the sample fragment is from a subject with cancer. In some embodiments, applying the sample state vector to the classifier generates at least one of a cancer probability and a non-cancer probability. In some embodiments, the method further comprising generating a cancer status score based on at least one of the cancer probability and the non-cancer probability.

In another aspect, the present disclosure provides a method for determining whether a test subject has cancer, the method comprising: accessing a model obtained by a training process with a cancer set of fragments from one or more training subjects with cancer and a non-cancer set of fragments from one or more training subjects without cancer, wherein both cancer set of fragments and the non-cancer set of fragments comprise a plurality of training fragments, wherein the training process comprises: for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, for each of a plurality of CpG sites in a reference genome: quantifying a count of hypomethylated training fragments which overlap the CpG site and a count of hypermethylated training fragments which overlap the CpG site; and generating a hypomethylation score and a hypermethylation score based on the count of hypomethylated training fragments and hypermethylated training fragments; for each training fragment, generating an aggregate hypomethylation score based on the hypomethylation score of the CpG sites in the training fragment and an aggregate hypermethylation score based on the hypermethylation score of the CpG sites in the training fragment; for each training subject: ranking the plurality of training fragments based on aggregate hypomethylation score and ranking the plurality of training fragments based on aggregate hypermethylation score; and generating a feature vector based on the ranking of the training fragments; obtaining training feature vectors for one or more training subjects without cancer and training feature vectors for the one or more training subjects with cancer; and training the model with the feature vectors for the one or more training subjects without cancer and the feature vectors for the one or more training subjects with cancer; and applying the model to a test feature vector corresponding to the test subject to determine whether the test subject has cancer.

In some embodiments, the threshold number is five or greater. In some embodiments, the threshold percentage is 80% or greater.

In some embodiments, for each CpG site in a reference genome quantifying a count of hypomethylated training fragments which overlap that CpG site and a count of hypermethylated training fragments which overlap that CpG site further comprises: quantifying a cancer count of hypomethylated training fragments from the one or more training subjects with cancer that overlap that CpG site and a non-cancer count of hypomethylated training fragments from the one or more training subjects without cancer that overlap that CpG site; and quantifying a cancer count of hypermethylated training fragments from the one or more training subjects with cancer that overlap that CpG site and a non-cancer count of hypermethylated training fragments from the one or more training subjects without cancer that overlap that CpG site.

In some embodiments, for each CpG site in a reference genome generating a hypomethylation score and a hypermethylation score based on the count of hypomethylated training fragments and hypermethylated training fragments further comprises: for generating the hypomethylation score, calculating a hypomethylation ratio of the cancer count of hypomethylated training fragments over a hypomethylation sum of the cancer count of hypomethylated training fragments and the non-cancer count of hypomethylated training fragments; and for generating the hypermethylation score, calculating a hypermethylation ratio of the cancer count of hypermethylated training fragments over a hypermethylation sum of the cancer count of hypermethylated training fragments and the non-cancer count of hypermethylated training fragments. In some embodiments, the hypomethylation and hypermethylation ratios are further calculated with a smoothing algorithm.

In some embodiments, for each CpG site in a reference genome generating a hypomethylation score and a hypermethylation score based on the count of hypomethylated training fragments and hypermethylated training fragments further comprises: for generating the hypomethylation score, calculating a hypomethylation log ratio of the cancer count of hypomethylated training fragments over the non-cancer count of hypomethylated training fragments; and for generating the hypermethylation score, calculating a hypermethylation log ratio of the cancer count of hypermethylated training fragments over the non-cancer count of hypermethylated training fragments. In some embodiments, the hypomethylation and hypermethylation ratios are further calculated with a smoothing algorithm. In some embodiments, for each training fragment, generating an aggregate hypomethylation score based on the hypomethylation score of the CpG sites in that training fragment and an aggregate hypermethylation score based on the hypermethylation score of the CpG sites in that training fragment further comprises identifying a maximum hypomethylation score of the CpG sites in that training fragment as the aggregate hypomethylation score and identifying a maximum hypermethylation score of the CpG sites in that training fragment as the aggregate hypermethylation score.

In some embodiments, for each training subject generating a training feature vector based on the ranking of the training fragments further comprises identifying a plurality of aggregate hypomethylation scores from the ranking and a plurality of aggregate hypermethylation scores from the ranking and generating a training feature vector comprising the plurality of aggregate hypomethylation scores and the plurality of hypermethylation scores.

In some embodiments, training the model with the training feature vectors from the one or more training subjects without cancer and the training feature vectors from the one or more training subjects with cancer is trained by a non-linear classifier.

In some embodiments, for each training subject, normalizing the training feature vector by an average length of that training subject's training fragments. In some embodiments, the method further comprises the step of obtaining the test feature vector corresponding to the test subject, wherein the step of obtaining the test feature vector comprises: obtaining sequence reads of a set of test fragments from the test subject; for each test fragment, determining whether that test fragment is hypomethylated or hypermethylated, wherein each of the hypomethylated and hypermethylated test fragments comprises at least a threshold number of CpG sites with at least a threshold percentage of the CpG sites being unmethylated or methylated, respectively, for each of a plurality of CpG sites in a reference genome: quantifying a count of hypomethylated test fragments which overlap the CpG site and a count of hypermethylated test fragments which overlap the CpG site; and generating a hypomethylation score and a hypermethylation score based on the count of hypomethylated test fragments and hypermethylated test fragments; for each test fragment, generating an aggregate hypomethylation score based on the hypomethylation score of the CpG sites in the test fragment and an aggregate hypermethylation score based on the hypermethylation score of the CpG sites in the test fragment; for the test subject, ranking the plurality of test fragments based on aggregate hypomethylation score and ranking the plurality of test fragments based on aggregate hypermethylation score; and generating the test feature vector based on the ranking of the test fragments.

In some embodiments, applying the model to the test feature vector of the test subject to determine whether the test subject has cancer comprises: generating a cancer probability for the test subject based on the model; and comparing the cancer probability to a threshold probability to determine whether the test subject has cancer.

In some embodiments, the diagnostic model comprises a kernel logistic regression classifier.

In yet another aspect, the present disclosure provides a method for determining whether a test subject has cancer, the method comprising: accessing a model obtained by a training process with a cancer set of training fragments from one or more training subjects with cancer and a non-cancer set of training fragments from one or more training subjects without cancer, wherein both cancer set of training fragments and the non-cancer set of training fragments comprise a plurality of training fragments, wherein the training process comprises: for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, for each training subject, generating a training feature vector based on the hypomethylated training fragments and hypermethylated training fragments, and training the model with the training feature vectors from the one or more training subjects without cancer and the feature vectors from the one or more training subjects with cancer; and applying the model to a test feature vector corresponding to the test subject to determine whether the test subject has cancer.

In some embodiments, for each training subject, generating the training feature vector comprises: for each of a plurality of CpG sites in a reference genome: quantifying a count of hypomethylated training fragments which overlap the CpG site and a count of hypermethylated training fragments which overlap the CpG site; and generating a hypomethylation score and a hypermethylation score based on the count of hypomethylated training fragments and hypermethylated training fragments; for each training fragment for the training subject, generating an aggregate hypomethylation score based on the hypomethylation score of the CpG sites in the training fragment and an aggregate hypermethylation score based on the hypermethylation score of the CpG sites in the training fragment; and ranking the plurality of training fragments of the training subject based on aggregate hypomethylation score and ranking the plurality of training fragments of that training subject based on aggregate hypermethylation score, wherein the training feature vector for the training subject is based on the ranking based on aggregate hypomethylation score and the ranking based on aggregate hypermethylation score.

In some embodiments, the method further comprises the step of obtaining the test feature vector corresponding to the test subject, wherein the step of obtaining the test feature vector comprises: obtaining sequence reads of a set of test fragments from the test subject; for each test fragment, determining whether that test fragment is hypomethylated or hypermethylated, wherein each of the hypomethylated and hypermethylated test fragments comprises at least a threshold number of CpG sites with at least a threshold percentage of the CpG sites being unmethylated or methylated, respectively, for each of a plurality of CpG sites in a reference genome: quantifying a count of hypomethylated test fragments which overlap the CpG site and a count of hypermethylated test fragments which overlap the CpG site; and generating a hypomethylation score and a hypermethylation score based on the count of hypomethylated test fragments and hypermethylated test fragments; for each test fragment, generating an aggregate hypomethylation score based on the hypomethylation score of the CpG sites in the test fragment and an aggregate hypermethylation score based on the hypermethylation score of the CpG sites in the test fragment; for the test subject, ranking the plurality of test fragments based on aggregate hypomethylation score and ranking the plurality of test fragments based on aggregate hypermethylation score; and generating the test feature vector based on the ranking of the test fragments. In some embodiments, applying the model to the test feature vector of the test subject to determine whether the test subject has cancer comprises: generating a cancer probability for the test subject based on the model; and comparing the cancer probability to a threshold probability to determine that the subject has cancer. In some embodiments, the diagnostic model comprises a kernel logistic regression classifier.

In one aspect, the present disclosure provides a method for predicting whether a test fragment from a test subject suspected of having cancer has an anomalous methylation pattern, the method comprising: accessing a data structure comprising counts of strings of CpG sites within a reference genome and their respective methylation states from a set of training fragments; generating a test state vector for a test fragment, wherein the test state vector comprises a test genomic location within the reference genome and a methylation state for each of a plurality of CpG sites in the test fragment, wherein each methylation state is determined to be one of: methylated, unmethylated, and indeterminate; calculating a test probability for the test state vector based on the counts stored in the data structure; sampling a subset of possible methylation state vectors from the test genomic location that are of a same length as the test state vector; for each of the sampled possible methylation state vectors, calculating a probability corresponding to the sampled possible methylation state vectors based at least in part on the counts stored in the data structure; calculating a proportion of the sampled possible methylation state vectors corresponding to a calculated probability less than or equal to the test probability; based on the calculated proportion, generating an estimated score for the test fragment; and determining, based on the estimated score, whether the test fragment is likely to have an anomalous methylation pattern.

In some embodiments, the method further comprises: filtering the test fragment by comparing the estimated score to a threshold score, the threshold score selected such that test fragments associated with an estimated score below the threshold score are more likely to include an anomalous methylation pattern. In some embodiments, the method further comprises: in response to determining that the test fragment is likely to have an anomalous methylation pattern, computing an exhaustive score for the test fragment of the test state vector relative to the set of training fragments, wherein the exhaustive score is based on the test probability and the probabilities of the plurality of possible methylation state vectors; and determining whether the test fragment has an anomalous methylation pattern based on the exhaustive score.

In some embodiments, the method further comprises: applying a classifier to the test state vector, the classifier trained with a first set of training fragments from one or more training subjects with cancer and a second set of training fragments from one or more training subjects without cancer, wherein the classifier can be used to determine whether the test subject has cancer.

In another aspect, the present disclosure provides a non-transitory computer readable storage medium storing executed instructions for detecting an anomalous methylation pattern in a cell-free deoxyribonucleic acid (cfDNA) sample fragment that, when executed by a hardware processor, cause the hardware processor to perform steps comprising: accessing a data structure comprising counts of strings of CpG sites within a reference genome and their respective methylation states from a set of training fragments; generating a sample state vector for a sample fragment comprising a sample genomic location within the reference genome and a methylation state for each of a plurality of CpG sites in the sample fragment, each methylation state determined to be methylated or unmethylated; enumerating a plurality of possibilities of methylation states from the sample genomic location that are of a same length as the sample state vector; for each of the possibilities, calculating a probability by accessing the counts stored in the data structure; identifying the possibility that matches the sample state vector and correspondingly the calculated probability as a sample probability; based on the sample probability, generating a score for the sample fragment of the sample state vector relative to the set of training fragments; and determining whether or not the sample fragment has an anomalous methylation pattern based on the generated score.

In some embodiments, each of the strings of CpG sites comprises the methylation state for each of the CpG sites at a plurality of genomic locations within the reference genome, wherein each of the methylation states is determined to be methylated or unmethylated.

In some embodiments, the steps further comprise: building the data structure from the set of training fragments and comprising: for each training fragment in the set of training fragments, generating a training state vector comprising a known genomic location within the reference genome and the methylation state for each of the plurality of CpG sites in the training fragment, each methylation state determined to be methylated or unmethylated; determining a plurality of strings, wherein each string is a portion of the training state vector, quantifying a count of each string from the training state vectors; and storing a plurality of counts for each string in the data structure.

In some embodiments, the step of determining whether the sample fragment has an anomalous methylation pattern based on the generated score further comprises determining whether the generated score for the sample fragment is below a threshold score, wherein the threshold score indicates a degree of confidence that the sample fragment has an anomalous methylation pattern. In some embodiments, the threshold score is 0.1 or smaller.

In some embodiments, the set of training fragments comprise training fragments from one or more healthy subjects, wherein the one or more healthy subjects lack a specific medical disorder and wherein the sample fragment is determined to be anomalously methylated relative to the set of training fragments from the one or more healthy subjects.

In some embodiments, generating the score for the sample fragment comprises: identifying calculated probabilities for possibilities of methylation states that are less than the sample probability; and generating the score for the sample fragment by summing all the identified probabilities with the sample probability.

In some embodiments, the step of calculating a probability by accessing the counts stored in the data structure for each of the possibilities comprises: for each of a plurality of conditional elements, wherein each conditional element is a conditional probability considering a subset of CpG sites in the possibility, calculating a Markov chain probability of an order with the plurality of counts stored in the data structure by the steps comprising: identifying a first count of number of strings matching that conditional element; identifying a second count of number of strings matching that conditional element's prior methylation states up to the whole number length; and calculating the Markov chain probability by dividing the first count by the second count. In some embodiments, the order is selected from the group consisting of: 1, 2, 3, 4, 5, 6, 7, 8, 9, 10, 11, 12, 13, 14, and 15. In some embodiments, the step of calculating a Markov chain probability of an order with the plurality of counts stored in the data structure further comprises implementing a smoothing algorithm.

In some embodiments, the sample state vector is partitioned into a plurality of windows comprising a first window and a second window, wherein the first window and the second window are two different portions of the sample fragment; wherein identifying the possibility that matches the sample state vector and correspondingly the calculated probability as the sample probability comprises identifying a first possibility with a first sample probability that matches the first window and a second possibility with a second sample probability that matches the second window; and wherein the generated score is based on one of the first sample probability and the second sample probability.

In some embodiments, the steps further comprise filtering a plurality of sample fragments based on the generated scores for each sample fragment, resulting in a subset of sample fragments having anomalous methylation patterns.

In some embodiments, the steps further comprise identifying the sample fragment as hypermethylated when the sample fragment comprises at least a threshold number of CpG sites with more than a threshold percentage of the CpG sites being methylated. In some embodiments, the threshold number of CpG sites is 5 or more CpG sites, and wherein the threshold percentage of CpG sites methylated is 80% or greater.

In some embodiments, the steps further comprise identifying the sample fragment as hypomethylated when the sample fragment comprises at least a threshold number of CpG sites with more than a threshold percentage of the CpG sites being unmethylated. In some embodiments, the threshold number of CpG sites is 5 or more CpG sites, and wherein the threshold percentage of CpG sites unmethylated is 80% or greater.

In some embodiments, the steps further comprise: applying the sample state vector to a classifier, trained with a cancer set of training fragments from one or more subjects with cancer and a non-cancer set of training fragments from one or more subjects without cancer, wherein the classifier can be used to determine whether the sample fragment is from a subject with cancer. In some embodiments, the step of applying the sample state vector to the classifier generates at least one of a cancer probability and a non-cancer probability. In some embodiments, the steps further comprise generating a cancer status score based on at least one of the cancer probability and the non-cancer probability.

In yet another aspect, the present disclosure provides a non-transitory computer readable storage medium storing executed instructions for determining whether a test subject has cancer that, when executed by a hardware processor, cause the hardware processor to perform steps comprising: accessing a model obtained by a training process with a cancer set of fragments from one or more training subjects with cancer and a non-cancer set of fragments from one or more training subjects without cancer, wherein both cancer set of fragments and the non-cancer set of fragments comprise a plurality of training fragments, wherein the training process comprises: for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, for each of a plurality of CpG sites in a reference genome: quantifying a count of hypomethylated training fragments which overlap the CpG site and a count of hypermethylated training fragments which overlap the CpG site; and generating a hypomethylation score and a hypermethylation score based on the count of hypomethylated training fragments and hypermethylated training fragments; for each training fragment, generating an aggregate hypomethylation score based on the hypomethylation score of the CpG sites in the training fragment and an aggregate hypermethylation score based on the hypermethylation score of the CpG sites in the training fragment; for each training subject: ranking the plurality of training fragments based on aggregate hypomethylation score and ranking the plurality of training fragments based on aggregate hypermethylation score; and generating a feature vector based on the ranking of the training fragments; obtaining training feature vectors for the one or more training subjects without cancer and training feature vectors for the one or more training subjects with cancer; training the model with the training feature vectors for the one or more training subjects without cancer and the training feature vectors for the one or more training subjects with cancer; and applying the model to a test feature vector corresponding to the test subject to determine whether the test subject has cancer. In some embodiments, the threshold number is five or greater. In some embodiments, the threshold percentage is 80% or greater.

In some embodiments, for each CpG site in a reference genome, quantifying a count of hypomethylated training fragments which overlap that CpG site and a count of hypermethylated training fragments which overlap that CpG site further comprises: quantifying a cancer count of hypomethylated training fragments from the one or more training subjects with cancer that overlap that CpG site and a non-cancer count of hypomethylated training fragments from the one or more training subjects without cancer that overlap that CpG site; and quantifying a cancer count of hypermethylated training fragments from the one or more training subjects with cancer that overlap that CpG site and a non-cancer count of hypermethylated training fragments from the one or more training subjects without cancer that overlap that CpG site. In some embodiments, for each CpG site in a reference genome, generating a hypomethylation score and a hypermethylation score based on the count of hypomethylated training fragments and hypermethylated training fragments further comprises: for generating the hypomethylation score, calculating a hypomethylation ratio of the cancer count of hypomethylated training fragments over a hypomethylation sum of the cancer count of hypomethylated training fragments and the non-cancer count of hypomethylated training fragments; and for generating the hypermethylation score, calculating a hypermethylation ratio of the cancer count of hypermethylated training fragments over a hypermethylation sum of the cancer count of hypermethylated training fragments and the non-cancer count of hypermethylated training fragments.

In some embodiments, the hypomethylation and hypermethylation ratios are further calculated with a smoothing algorithm. In some embodiments, generating a hypomethylation score and a hypermethylation score based on the count of hypomethylated training fragments and hypermethylated training fragments further comprises: for generating the hypomethylation score, calculating a hypomethylation log ratio of the cancer count of hypomethylated training fragments over the non-cancer count of hypomethylated training fragments; and for generating the hypermethylation score, calculating a hypermethylation log ratio of the cancer count of hypermethylated training fragments over the non-cancer count of hypermethylated training fragments. In some embodiments, the hypomethylation and hypermethylation ratios are further calculated with a smoothing algorithm. In some embodiments, for each training fragment, generating an aggregate hypomethylation score based on the hypomethylation score of the CpG sites in that training fragment and an aggregate hypermethylation score based on the hypermethylation score of the CpG sites in that training fragment further comprises identifying a maximum hypomethylation score of the CpG sites in that training fragment as the aggregate hypomethylation score and identifying a maximum hypermethylation score of the CpG sites in that training fragment as the aggregate hypermethylation score.

In some embodiments, for each training subject generating a training feature vector based on the ranking of the training fragments further comprises identifying a plurality of aggregate hypomethylation scores from the ranking and a plurality of aggregate hypermethylation scores from the ranking and generating a training feature vector comprising the plurality of aggregate hypomethylation scores and the plurality of hypermethylation scores.

In some embodiments, training the model with the training feature vectors from the one or more training subjects without cancer and the training feature vectors from the one or more training subjects with cancer is trained by a non-linear classifier.

In some embodiments, the steps further comprise, for each training subject, normalizing the training feature vector by an average length of that training subject's training fragments.

In some embodiments, the steps further comprise: obtaining the test feature vector corresponding to the test subject, wherein the step of obtaining the test feature vector comprises: obtaining sequence reads of a set of test fragments from the test subject; for each test fragment, determining whether that test fragment is hypomethylated or hypermethylated, wherein each of the hypomethylated and hypermethylated test fragments comprises at least a threshold number of CpG sites with at least a threshold percentage of the CpG sites being unmethylated or methylated, respectively, for each of a plurality of CpG sites in a reference genome: quantifying a count of hypomethylated test fragments which overlap the CpG site and a count of hypermethylated test fragments which overlap the CpG site; and generating a hypomethylation score and a hypermethylation score based on the count of hypomethylated test fragments and hypermethylated test fragments; for each test fragment, generating an aggregate hypomethylation score based on the hypomethylation score of the CpG sites in the test fragment and an aggregate hypermethylation score based on the hypermethylation score of the CpG sites in the test fragment; for the test subject, ranking the plurality of test fragments based on aggregate hypomethylation score and ranking the plurality of test fragments based on aggregate hypermethylation score; and generating the test feature vector based on the ranking of the test fragments.

In some embodiments, applying the model to the test feature vector of the test subject to determine whether the test subject has cancer comprises: generating a cancer probability for the test subject based on the model; and comparing the cancer probability to a threshold probability to determine whether the test subject has cancer.

In yet another aspect, the present disclosure provides a non-transitory computer readable storage medium storing executed instructions for determining whether a test subject has cancer that, when executed by a hardware processor, cause the hardware processor to perform steps comprising: accessing a model obtained by a training process with a cancer set of training fragments from one or more training subjects with cancer and a non-cancer set of training fragments from one or more training subjects without cancer, wherein both cancer set of training fragments and the non-cancer set of training fragments comprise a plurality of training fragments, wherein the training process comprises: for each training fragment, determining whether that training fragment is hypomethylated or hypermethylated, wherein each of the hypomethylated and hypermethylated training fragments comprises at least a threshold number of CpG sites with at least a threshold percentage of the CpG sites being unmethylated or methylated, respectively, for each training subject, generating a training feature vector based on the hypomethylated training fragments and hypermethylated training fragments, and training the model with the training feature vectors from the one or more training subjects without cancer and the feature vectors from the one or more training subjects with cancer; and applying the model to a test feature vector corresponding to the test subject to determine whether the test subject has cancer.

In some embodiments, for each training subject, generating the training feature vector comprises: for each of a plurality of CpG sites in a reference genome: quantifying a count of hypomethylated training fragments which overlap the CpG site and a count of hypermethylated training fragments which overlap the CpG site; and generating a hypomethylation score and a hypermethylation score based on the count of hypomethylated training fragments and hypermethylated training fragments; for each training fragment for the training subject, generating an aggregate hypomethylation score based on the hypomethylation score of the CpG sites in the training fragment and an aggregate hypermethylation score based on the hypermethylation score of the CpG sites in the training fragment; and ranking the plurality of training fragments of the training subject based on aggregate hypomethylation score and ranking the plurality of training fragments of that training subject based on aggregate hypermethylation score, wherein the training feature vector for the training subject is based on the ranking based on aggregate hypomethylation score and the ranking based on aggregate hypermethylation score.

In some embodiments, the steps further comprise: obtaining the test feature vector corresponding to the test subject, wherein the step of obtaining the test feature vector comprises: obtaining sequence reads of a set of test fragments from the test subject; for each test fragment, determining whether that test fragment is hypomethylated or hypermethylated, wherein each of the hypomethylated and hypermethylated test fragments comprises at least a threshold number of CpG sites with at least a threshold percentage of the CpG sites being unmethylated or methylated, respectively, for each of a plurality of CpG sites in a reference genome: quantifying a count of hypomethylated test fragments which overlap the CpG site and a count of hypermethylated test fragments which overlap the CpG site; and generating a hypomethylation score and a hypermethylation score based on the count of hypomethylated test fragments and hypermethylated test fragments; for each test fragment, generating an aggregate hypomethylation score based on the hypomethylation score of the CpG sites in the test fragment and an aggregate hypermethylation score based on the hypermethylation score of the CpG sites in the test fragment; for the test subject, ranking the plurality of test fragments based on aggregate hypomethylation score and ranking the plurality of test fragments based on aggregate hypermethylation score; and generating the test feature vector based on the ranking of the test fragments. In some embodiments, applying the model to the test feature vector of the test subject to determine whether the test subject has cancer comprises: generating a cancer probability for the test subject based on the model; and comparing the cancer probability to a threshold probability to determine that the subject has cancer.

In one aspect, the present disclosure provides a non-transitory computer readable storage medium storing executed instructions for determining whether a test fragment from a test subject suspected of having cancer has an anomalous methylation pattern that, when executed by a hardware processor, cause the hardware processor to perform steps comprising accessing a data structure comprising counts of strings of CpG sites within a reference genome and their respective methylation states from a set of training fragments; generating a test state vector for a test fragment, wherein the test state vector comprises a test genomic location within the reference genome and a methylation state for each of a plurality of CpG sites in the test fragment, wherein each methylation state is determined to be one of: methylated, unmethylated, and indeterminate; calculating a test probability for the test state vector based on the counts stored in the data structure; sampling a subset of possible methylation state vectors from the test genomic location that are of a same length as the test state vector; for each of the sampled possible methylation state vectors, calculating a probability corresponding to the sampled possible methylation state vectors based at least in part on the counts stored in the data structure; calculating a proportion of the sampled possible methylation state vectors corresponding to a calculated probability less than or equal to the test probability; based on the calculated proportion, generating an estimated score for the test fragment; and determining, based on the estimated score, whether the test fragment is likely to have an anomalous methylation pattern.

In some embodiments, the steps further comprise: filtering the test fragment by comparing the estimated score to a threshold score, the threshold score selected such that test fragments associated with an estimated score below the threshold score are more likely to include an anomalous methylation pattern. In some embodiments, the steps further comprise: in response to determining that the test fragment is likely to have an anomalous methylation pattern, computing an exhaustive score for the test fragment of the test state vector relative to the set of training fragments, wherein the exhaustive score is based on the test probability and the probabilities of the plurality of possible methylation state vectors; and determining whether the test fragment has an anomalous methylation pattern based on the exhaustive score. In some embodiments, the steps further comprise: applying a classifier to the test state vector, the classifier trained with a first set of training fragments from one or more training subjects with cancer and a second set of training fragments from one or more training subjects without cancer, wherein the classifier can be used to determine whether the test subject has cancer.

In another aspect, the present disclosure provides a non-transitory computer readable storage medium storing executable instructions that, when executed by a hardware processor, cause the processor to implement a classifier to diagnose cancer, wherein the classifier is generated by the process comprising: a. obtaining sequence reads of a cancer set of fragments from one or more subjects with cancer and sequence reads of a non-cancer set of fragments from one or more subjects without cancer, wherein both cancer set of fragments and the non-cancer set of fragments comprise a plurality of sample fragments; b. for each fragment, determining whether the fragment is hypomethylated or hypermethylated, wherein hypomethylated and hypermethylated fragments comprise at least a threshold number of CpG sites with at least a threshold percentage of the CpG sites being unmethylated or methylated, respectively; c. for each of a plurality of CpG sites in a reference genome: i. quantifying a count of hypomethylated fragments which overlap the CpG site and a count of hypermethylated fragments which overlap the CpG site; and ii. generating a hypomethylation score and a hypermethylation score based on the count of hypomethylated fragments and hypermethylated fragments; d. for each subject: i. ranking the plurality of fragments based on aggregate hypomethylation score and ranking the plurality of fragments based on aggregate hypermethylation score; and ii. generating a feature vector based on the ranking of the fragments; e. training a diagnostic model based on the generated feature vectors from the one or more subjects with cancer and the generated features vectors from the one or more subjects without cancer, the diagnostic model configured to receive a set of test feature vectors from a test subject and to output a likelihood of cancer based on the set of test feature vectors from the test subject; and f. storing a set of parameters representative of the diagnostic model on the non-transitory computer readable storage medium.

In some embodiments, the diagnostic model comprises a neural network having a plurality of layers including an input layer for receiving the feature vectors from the one or more subjects with cancer and from the one or more subjects without cancer and an output layer for indicating a likelihood of cancer based on the feature vectors. In some embodiments, the diagnostic model further comprises updating the neural network by repeatedly backpropagating one or more error terms obtained by applying a training example from a plurality of training examples to the diagnostic model and computing a loss function, wherein the plurality of layers are updated based on the computed loss function. In some embodiments, the diagnostic model comprises a kernel logistic regression classifier. In some embodiments, determining whether a fragment is hypomethylated or hypermethylated comprises: a. accessing a data structure comprising counts of strings of CpG sites within a reference genome and their respective methylation states from a set of training fragments; b. generating a state vector for the fragment comprising a genomic location within the reference genome and a methylation state for each of a plurality of CpG sites in the fragment, each methylation state determined to be methylated or unmethylated; c. enumerating a plurality of possible methylation states from the genomic location that are of a same length as the state vector; d. for each possible methylation state, calculating a corresponding probability based on the counts of strings stored in the data structure; e. identifying the possible methylation state that matches the state vector and the calculated probability corresponding to the identified possible methylation state; f generating a score for the fragment of the state vector relative to the set of training fragments based on the identified calculated probability; and g. determining whether the fragment is one of hypomethylated and hypermethylated based on the generated score. In some embodiments, the diagnostic model is applied to a test feature vector of a test subject, the diagnostic model configured to output a cancer probability for the test subject and to compare the outputted cancer probability to a threshold probability to determine whether the test subject has cancer.

In another aspect, the present disclosure provides a non-transitory computer readable storage medium storing executable instructions that, when executed by a hardware processor, cause the processor to implement a classifier to diagnose cancer, wherein the classifier is generated by the process comprising: a. obtaining sequence reads of a cancer set of fragments from one or more subjects with cancer and sequence reads of a non-cancer set of fragments from one or more subjects without cancer, wherein both cancer set of fragments and the non-cancer set of fragments comprise a plurality of sample fragments; b. for each fragment, determining whether the fragment has an anomalous methylation pattern, thereby obtaining a set of anomalously methylated fragments; c. for each anomalously methylated fragment, determining whether that the anomalously methylated fragment is hypomethylated or hypermethylated, wherein hypomethylated and hypermethylated fragments comprise at least a threshold number of CpG sites with at least a threshold percentage of the CpG sites being unmethylated or methylated, respectively; d. for each of a plurality of CpG sites in a reference genome: i. quantifying a count of hypomethylated fragments which overlap the CpG site and a count of hypermethylated fragments which overlap the CpG site; and ii. generating a hypomethylation score and a hypermethylation score based on the count of hypomethylated fragments and hypermethylated fragments; e. for each subject: i. ranking the plurality of fragments based on aggregate hypomethylation score and ranking the plurality of fragments based on aggregate hypermethylation score; and ii. generating a feature vector based on the ranking of the fragments; f. training a diagnostic model based on the generated feature vectors from the one or more subjects with cancer and the generated features vectors from the one or more subjects without cancer, the diagnostic model configured to receive a set of test feature vectors from a test subject and to output a likelihood of cancer based on the set of test feature vectors from the test subject; and g. storing a set of parameters representative of the diagnostic model on the non-transitory computer readable storage medium.

In some embodiments, the diagnostic model comprises a neural network having a plurality of layers including an input layer for receiving the feature vectors from the one or more subjects with cancer and from the one or more subjects without cancer and an output layer for indicating a likelihood of cancer based on the feature vectors. In some embodiments, the diagnostic model further comprises updating the neural network by repeatedly backpropagating one or more error terms obtained by applying a training example from a plurality of training examples to the diagnostic model and computing a loss function, wherein the plurality of layers are updated based on the computed loss function. In some embodiments, the diagnostic model comprises a kernel logistic regression classifier. In some embodiments, determining whether a fragment is anomalously methylated comprises: a. accessing a data structure comprising counts of strings of CpG sites within a reference genome and their respective methylation states from a set of training fragments; b. generating a state vector for the fragment comprising a genomic location within the reference genome and a methylation state for each of a plurality of CpG sites in the fragment, each methylation state determined to be methylated or unmethylated; c. enumerating a plurality of possible methylation states from the genomic location that are of a same length as the state vector; d. for each possible methylation state, calculating a corresponding probability based on the counts of strings stored in the data structure; e. identifying the possible methylation state that matches the state vector and the calculated probability corresponding to the identified possible methylation state; f generating a score for the fragment of the state vector relative to the set of training fragments based on the identified calculated probability; and g. determining whether the fragment is anomalously methylated based on the generated score. In some embodiments, the diagnostic model is applied to a test feature vector of a test subject, the diagnostic model configured to output a cancer probability for the test subject and to compare the outputted cancer probability to a threshold probability to determine whether the test subject has cancer.

BRIEF DESCRIPTION OF DRAWINGS

FIGS. 1C and 1D show three graphs of data validating consistency of sequencing from a control group.

FIG. 2 is a flowchart describing a process of creating a data structure for a control group, according to an embodiment.

FIG. 5 is an illustration of an example p-value score calculation, according to an embodiment.

FIGS. 7A-7C are graphs showing the cancer log-odds ratio determined for various cancers across different stages of cancer.

Figure 1A:
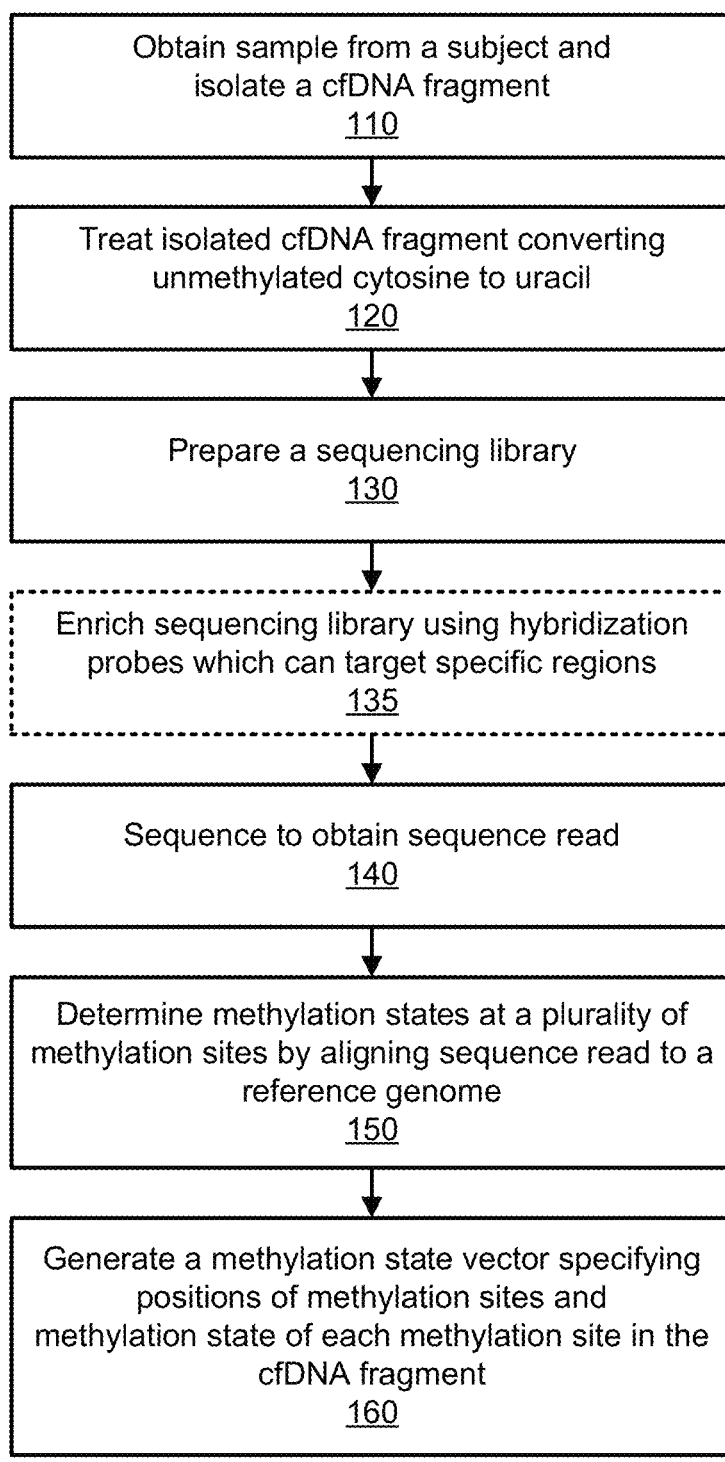
FIG. 1A is a flowchart describing a process of sequencing a fragment of cell-free (cf) DNA to obtain a methylation state vector, according to an embodiment.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

I. Overview

In accordance with the present invention, cfDNA fragments from a test subject are treated to convert unmethylated cytosines to uracils, sequenced and the sequence reads compared to a reference genome to identify the methylation states at one or more CpG sites within the fragments. Identification of anomalously methylated cfDNA fragments, in comparison to healthy subjects, may provide insight into a subject's cancer status. As is well known in the art, DNA methylation anomalies (compared to healthy controls) can cause different effects, which may contribute to cancer. Various challenges arise in the identification of anomalously methylated cfDNA fragments. First off, determining one or more cfDNA fragments to be anomalously methylated only holds weight in comparison with a group of control subjects with fragments assumed to be normally methylated. Additionally, among a group of control subjects methylation state can vary which can be difficult to account for when determining a subject's cfDNA to be anomalously methylated. On another note, methylation of a cytosine at a CpG site causally influences methylation at a subsequent CpG site. To encapsulate this dependency is a challenge in itself.

Methylation typically occurs in deoxyribonucleic acid (DNA) when a hydrogen atom on the pyrimidine ring of a cytosine base is converted to a methyl group, forming 5-methylcytosine. In particular, methylation tends to occur at dinucleotides of cytosine and guanine referred to herein as "CpG sites". In other instances, methylation may occur at a cytosine not part of a CpG site or at another nucleotide that's not cytosine; however, these are rarer occurrences. In this present disclosure, methylation is discussed in reference to CpG sites for the sake of clarity. Anomalous cfDNA fragment methylation may further be identified as hypermethylation or hypomethylation, both of which may be indicative of cancer status.

Those of skill in the art will appreciate that the principles described herein are equally applicable for the detection of methylation in a non-CpG context, including non-cytosine methylation. In such embodiments, the wet laboratory assay used to detect methylation may vary from those described herein. Further, the methylation state vectors may contain elements that are generally vectors of sites where methylation has or has not occurred (even if those cites are not CpG sites specifically). With that substitution, the remainder of the processes described herein are the same, and consequently the inventive concepts described herein are applicable to those other forms of methylation.

The term "cell free nucleic acid," "cell free DNA," or "cfDNA" refers to nucleic acid fragments, or DNA fragments, that circulate in a fluid from an individual's body (e.g., bloodstream) and originate from one or more healthy cells and/or from one or more cancer cells. Additionally cfDNA may come from other sources such as viruses, fetuses, etc.

The term "circulating tumor DNA" or "ctDNA" refers to nucleic acid fragments that originate from tumor cells or other types of cancer cells, which may be released into a fluid from an individual's body (e.g., bloodstream) as result of biological processes such as apoptosis or necrosis of dying cells or actively released by viable tumor cells.

The term "individual" refers to a human individual. The term "healthy individual" refers to an individual presumed to not have a cancer or disease. The term "subject" refers to an individual who is known to have, or potentially has, a cancer or disease.

The term "sequence reads" refers to nucleotide sequences read from a sample obtained from an individual. Sequence reads can be obtained through various methods known in the art.

The term "read segment" or "read" refers to any nucleotide sequences including sequence reads obtained from an individual and/or nucleotide sequences derived from the initial sequence read from a sample obtained from an individual.

II. Sample Processing

FIG. 1A is a flowchart describing a process 100 of sequencing a fragment of cell-free (cf) DNA to obtain a methylation state vector, according to an embodiment. In order to analyze DNA methylation, an analytics system first obtains 110 a sample from a subject comprising a plurality of cfDNA fragments. Generally, samples may be from healthy subjects, subjects known to have or suspected of having cancer, or subjects where no prior information is known. The test sample may be a sample selected from the group consisting of blood, plasma, serum, urine, fecal, and saliva samples. Alternatively, the test sample may comprise a sample selected from the group consisting of whole blood, a blood fraction, a tissue biopsy, pleural fluid, pericardial fluid, cerebral spinal fluid, and peritoneal fluid.

From the sample, the cfDNA fragments are treated to convert unmethylated cytosines to uracils. In one embodiment, the method uses a bisulfite treatment of the cfDNA fragments which converts the unmethylated cytosines to uracils without converting the methylated cytosines. For example, a commercial kit such as the EZ DNA Methylation™—Gold, EZ DNA Methylation™—Direct or an EZ DNA Methylation™—Lightning kit (available from Zymo Research Corp (Irvine, CA)) is used for the bisulfite conversion. In another embodiment, the conversion of unmethylated cytosines to uracils is accomplished using an enzymatic reaction. For example, the conversion can use a commercially available kit for conversion of unmethylated cytosines to uracils, such as APOBEC-Seq (NEBiolabs, Ipswich, MA).

From the converted cfDNA fragments, a sequencing library is prepared 130. Optionally, the sequencing library may be enriched 135 for cfDNA fragments, or genomic regions, that are informative for cancer status using a plurality of hybridization probes. The hybridization probes are short oligonucleotides capable of hybridizing to targeted cfDNA fragments, or to cfDNA fragments derived from one or more targeted regions, and enriching for those fragments or regions for subsequent sequencing and analysis. Hybridization probes may be used to perform a targeted, high-depth analysis of a set of specified CpG sites of interest. Once prepared, the sequencing library or a portion thereof can be sequenced to obtain a plurality of sequence reads. The sequence reads may be in a computer-readable, digital format for processing and interpretation by computer software.

From the sequence reads, the analytics system determines 150 a location and methylation state for each of one or more CpG sites based on alignment to a reference genome. The analytics system generates 160 a methylation state vector for each fragment specifying a location of the fragment in the reference genome (e.g., as specified by the position of the first CpG site in each fragment, or another similar metric), a number of CpG sites in the fragment, and the methylation state of each CpG site in the fragment whether methylated (e.g., denoted as M), unmethylated (e.g., denoted as U), or indeterminate (e.g., denoted as I). Observed states are states of methylated and unmethylated; whereas, an unobserved state is indeterminate. The methylation state vectors may be stored in temporary or persistent computer memory for later use and processing. Further, the analytics system may remove duplicate reads or duplicate methylation state vectors from a single subject. In an additional embodiment, the analytics system may determine that a certain fragment has one or more CpG sites that have an indeterminate methylation state. Indeterminate methylation states may originate from sequencing errors and/or disagreements between methylation states of a DNA fragment's complementary strands. The analytics system may decide to exclude such fragments or selectively include such fragments but build a model accounting for such indeterminate methylation states. One such model will be described below in conjunction with FIG. 4.

Figure 1B:
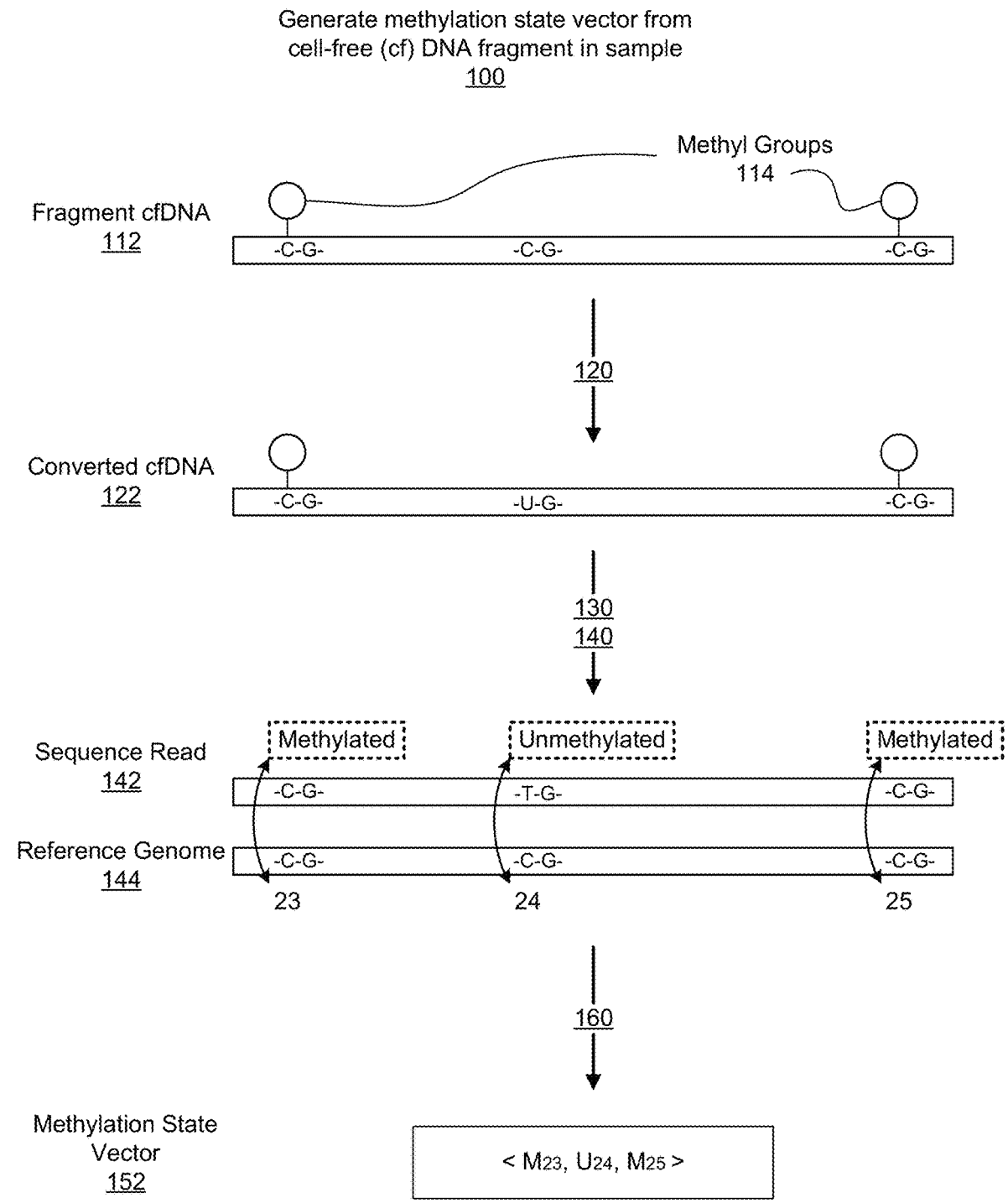
FIG. 1B is an illustration of the process of FIG. 1A of sequencing a fragment of cell-free (cf) DNA to obtain a methylation state vector, according to an embodiment.

FIG. 1B is an illustration of the process 100 of FIG. 1A of sequencing a cfDNA fragment to obtain a methylation state vector, according to an embodiment. As an example, the analytics system takes a cfDNA fragment 112. In this example, the cfDNA fragment 112 contains three CpG sites. As shown, the first and third CpG sites of the cfDNA fragment 112 are methylated 114. During the treatment step 120, the cfDNA fragment 112 is converted to generate a converted cfDNA fragment 122. During the treatment 120, the second CpG site which was unmethylated has its cytosine converted to uracil. However, the first and third CpG sites are not convert.

After conversion, a sequencing library 130 is prepared and sequenced 140 generating a sequence read 142. The analytics system aligns 150 the sequence read 142 to a reference genome 144. The reference genome 144 provides the context as to what position in a human genome the fragment cfDNA originates from. In this simplified example, the analytics system aligns 150 the sequence read such that the three CpG sites correlate to CpG sites 23, 24, and 25 (arbitrary reference identifiers used for convenience of description). The analytics system thus generates information both on methylation state of all CpG sites on the cfDNA fragment 112 and to which position in the human genome the CpG sites map. As shown, the CpG sites on sequence read 142 which were methylated are read as cytosines. In this example, the cytosine's appear in the sequence read 142 only in the first and third CpG site which allows one to infer that the first and third CpG sites in the original cfDNA fragment were methylated. Whereas, the second CpG site is read as a thymine (U is converted to T during the sequencing process), and thus, one can infer that the second CpG site was unmethylated in the original cfDNA fragment. With these two pieces of information, the methylation state and location, the analytics system generates 160 a methylation state vector 152 for the cfDNA fragment 112. In this example, the resulting methylation state vector 152 is <$M_{23}$, $U_{24}$, $M_{25}$>, wherein M corresponds to a methylated CpG site, U corresponds to an unmethylated CpG site, and the subscript number corresponds to a position of each CpG site in the reference genome.

Figure 1D:
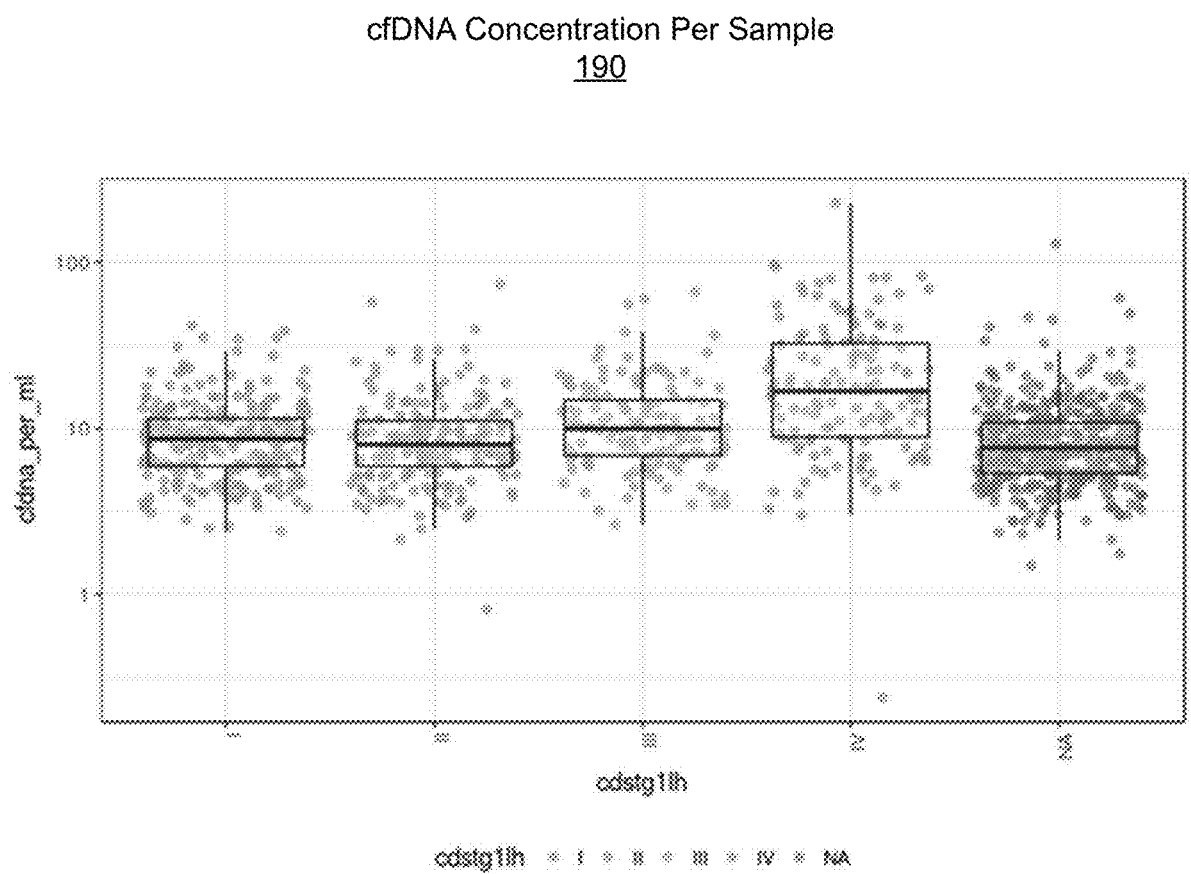

FIGS. 1C & 1D show three graphs of data validating consistency of sequencing from a control group. The first graph 170 shows conversion accuracy of conversion of unmethylated cytosines to uracil (step 120) on cfDNA fragment obtained from a test sample across subjects in varying stages of cancer—stage I, stage II, stage III, stage IV, and non-cancer. As shown, there was uniform consistency in converting unmethylated cytosines on cfDNA fragments into uracils. There was an overall conversion accuracy of 99.47% with a precision at ±0.024%. The second graph 180 shows mean coverage over varying stages of cancer. The mean coverage over all groups being ~34X mean across the genome coverage of DNA fragments, using only those confidently mapped to the genome are counted. The third graph 190 shows concentration of cfDNA per sample across varying stages of cancer.

III. Control Data Structure

III.A. Creation

FIG. 2 is a flowchart describing a process 200 of generating a data structure for a healthy control group, according to an embodiment. To create a healthy control group data structure, the analytics system receives a plurality of DNA fragments (e.g., cfDNA) from a plurality of subjects. A methylation state vector is identified for each fragment, for example via the process 100.

With each fragment's methylation state vector, the analytics system subdivides 210 the methylation state vector into strings of CpG sites. In one embodiment, the analytics system subdivides 210 the methylation state vector such that the resulting strings are all less than a given length. For example, a methylation state vector of length 11 may be subdivided into strings of length less than or equal to 3 would result in 9 strings of length 3, 10 strings of length 2, and 11 strings of length 1. In another example, a methylation state vector of length 7 being subdivided into strings of length less than or equal to 4 would result in 4 strings of length 4, 5 strings of length 3, 6 strings of length 2, and 7 strings of length 1. If a methylation state vector is shorter than or the same length as the specified string length, then the methylation state vector may be converted into a single string containing all of the CpG sites of the vector.

The analytics system tallies 220 the strings by counting, for each possible CpG site and possibility of methylation states in the vector, the number of strings present in the control group having the specified CpG site as the first CpG site in the string and having that possibility of methylation states. For example, at a given CpG site and considering string lengths of 3, there are 2^3 or 8 possible string configurations. At that given CpG site, for each of the 8 possible string configurations, the analytics system tallies 220 how many occurrences of each methylation state vector possibility come up in the control group. Continuing this example, this may involve tallying the following quantities: <$M_x$, $M_{x+1}$, $M_{x+2}$>, <$M_x$, $M_{x+1}$, $U_{x+2}$>, . . . , <$U_x$, $U_{x+1}$, $U_{x+2}$> for each starting CpG site x in the reference genome. The analytics system creates 230 the data structure storing the tallied counts for each starting CpG site and string possibility.

There are several benefits to setting an upper limit on string length. First, depending on the maximum length for a string, the size of the data structure created by the analytics system can dramatically increase in size. For instance, maximum string length of 4 means that every CpG site has at the very least 2^4 numbers to tally for strings of length 4. Increasing the maximum string length to 5 means that every CpG site has an additional 2^4 or 16 numbers to tally, doubling the numbers to tally (and computer memory required) compared to the prior string length. Reducing string size helps keep the data structure creation and performance (e.g., use for later accessing as described below), in terms of computational and storage, reasonable. Second, a statistical consideration to limiting the maximum string length is to avoid overfitting downstream models that use the string counts. If long strings of CpG sites do not, biologically, have a strong effect on the outcome (e.g., predictions of anomalousness that predictive of the presence of cancer), calculating probabilities based on large strings of CpG sites can be problematic as it requires a significant amount of data that may not be available, and thus would be too sparse for a model to perform appropriately. For example, calculating a probability of anomalousness/cancer conditioned on the prior 100 CpG sites would require counts of strings in the data structure of length 100, ideally some matching exactly the prior 100 methylation states. If only sparse counts of strings of length 100 are available, there will be insufficient data to determine whether a given string of length of 100 in a test sample is anomalous or not.

III.A. Data Structure Validation

Once the data structure has been created, the analytics system may seek to validate 240 the data structure and/or any downstream models making use of the data structure. One type of validation checks consistency within the control group's data structure. For example, if there are any outlier subjects, samples, and/or fragments within a control group, then the analytics system may perform various calculations to determine whether to exclude any fragments from one of those categories. In a representative example, the healthy control group may contain a sample that is undiagnosed but cancerous such that the sample contains anomalously methylated fragments. This first type of validation ensures that potential cancerous samples are removed from the healthy control group so as to not affect the control group's purity.

A second type of validation checks the probabilistic model used to calculate p-values with the counts from the data structure itself (i.e., from the healthy control group). A process for p-value calculation is described below in conjunction with FIG. 5. Once the analytics system generates a p-value for the methylation state vectors in the validation group, the analytics system builds a cumulative density function (CDF) with the p-values. With the CDF, the analytics system may perform various calculations on the CDF to validate the control group's data structure. One test uses the fact that the CDF should ideally be at or below an identity function, such that $CDF(x) \le x$. On the converse, being above the identity function reveals some deficiency within the probabilistic model used for the control group's data structure. For example, if 1/100 of fragments have a p-value score of 1/1000 meaning $CDF(1/1000)=1/100>1/1000$, then the second type of validation fails indicating an issue with the probabilistic model.

A third type of validation uses a healthy set of validation samples separate from those used to build the data structure, which tests if the data structure is properly built and the model works. An example process for carrying out this type of validation is described below in conjunction with FIG. 3. The third type of validation can quantify how well the healthy control group generalizes the distribution of healthy samples. If the third type of validation fails, then the healthy control group does not generalize well to the healthy distribution.

A fourth type of validation tests with samples from a non-healthy validation group. The analytics system calculates p-values and builds the CDF for the non-healthy validation group. With a non-healthy validation group, the analytics systems expects to see the CDF(x)>x for at least some samples or, stated differently, the converse of what was expected in the second type of validation and the third type of validation with the healthy control group and the healthy validation group. If the fourth type of validation fails, then this is indicative that the model is not appropriately identifying the anomalousness that it was designed to identify.

Figure 3:
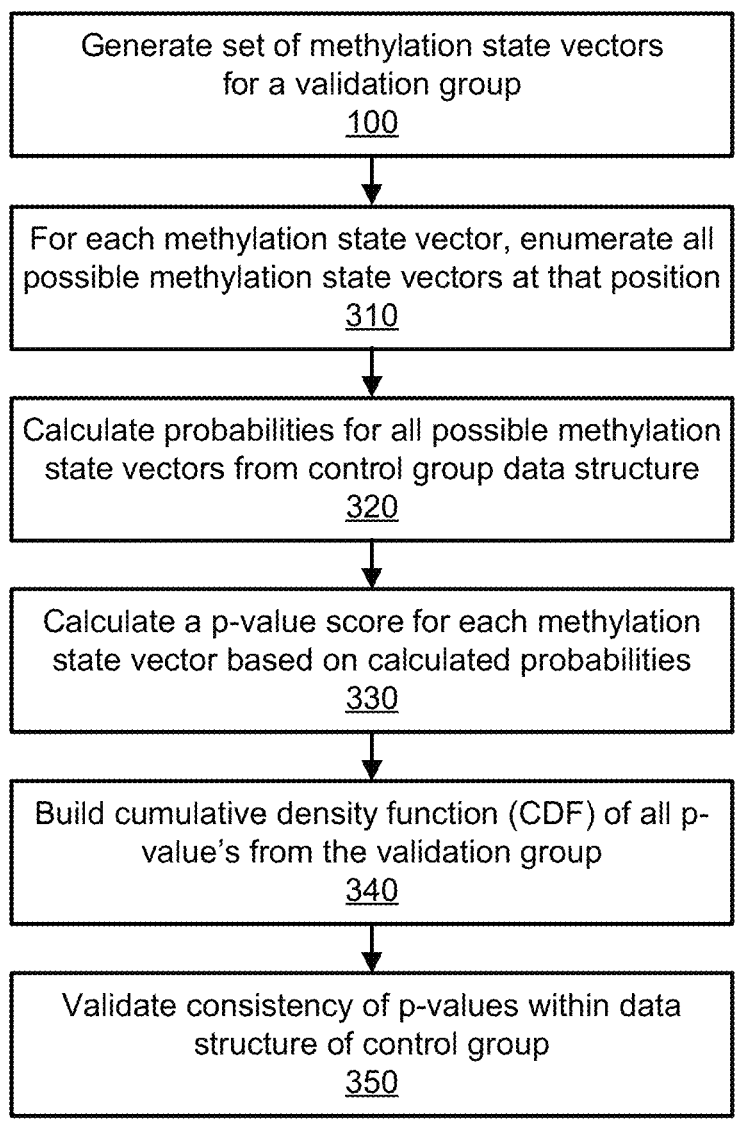
FIG. 3 is a flowchart describing an additional step of validating the data structure for the control group of FIG. 2, according to an embodiment.

FIG. 3 is a flowchart describing an additional step 240 of validating the data structure for the control group of FIG. 2, according to an embodiment. In this step 240 of validating the data structure, the analytics system utilizes a validation group with a supposedly similar composition of subjects, samples, and/or fragments as the control group. For example, if the analytics system selected healthy subjects without cancer for the control group, then the analytics system also uses healthy subjects without cancer in the validation group.

The analytics system takes the validation group and generates 100 a set of methylation state vectors as described in FIG. 1. The analytics system performs a p-value calculation for each methylation state vector from the validation group. The p-value calculation process will be further described in conjunction with FIGS. 4 & 5. For each possibility of methylation state vector, the analytics system calculates 320 a probability from the control group's data structure. Once the probabilities are calculated for the possibilities of methylation state vectors, the analytics system calculates 330 a p-value score for that methylation state vector based on the calculated probabilities. The p-value score represents an expectedness of finding that specific methylation state vector and other possible methylation state vectors having even lower probabilities in the control group. A low p-value score, thereby, generally corresponds to a methylation state vector which is relatively unexpected in comparison to other methylation state vectors within the control group, where a high p-value score generally corresponds to a methylation state vector which is relatively more expected in comparison to other methylation state vectors found in the control group. Once the analytics system generates a p-value score for the methylation state vectors in the validation group, the analytics system builds 340 a cumulative density function (CDF) with the p-value scores from the validation group. The CFD may be used in validation tests as described above elsewhere in this section.

IV. Identifying Fragments Having an Anomalous Methylation Pattern

IV.A. General Process

Figure 4:
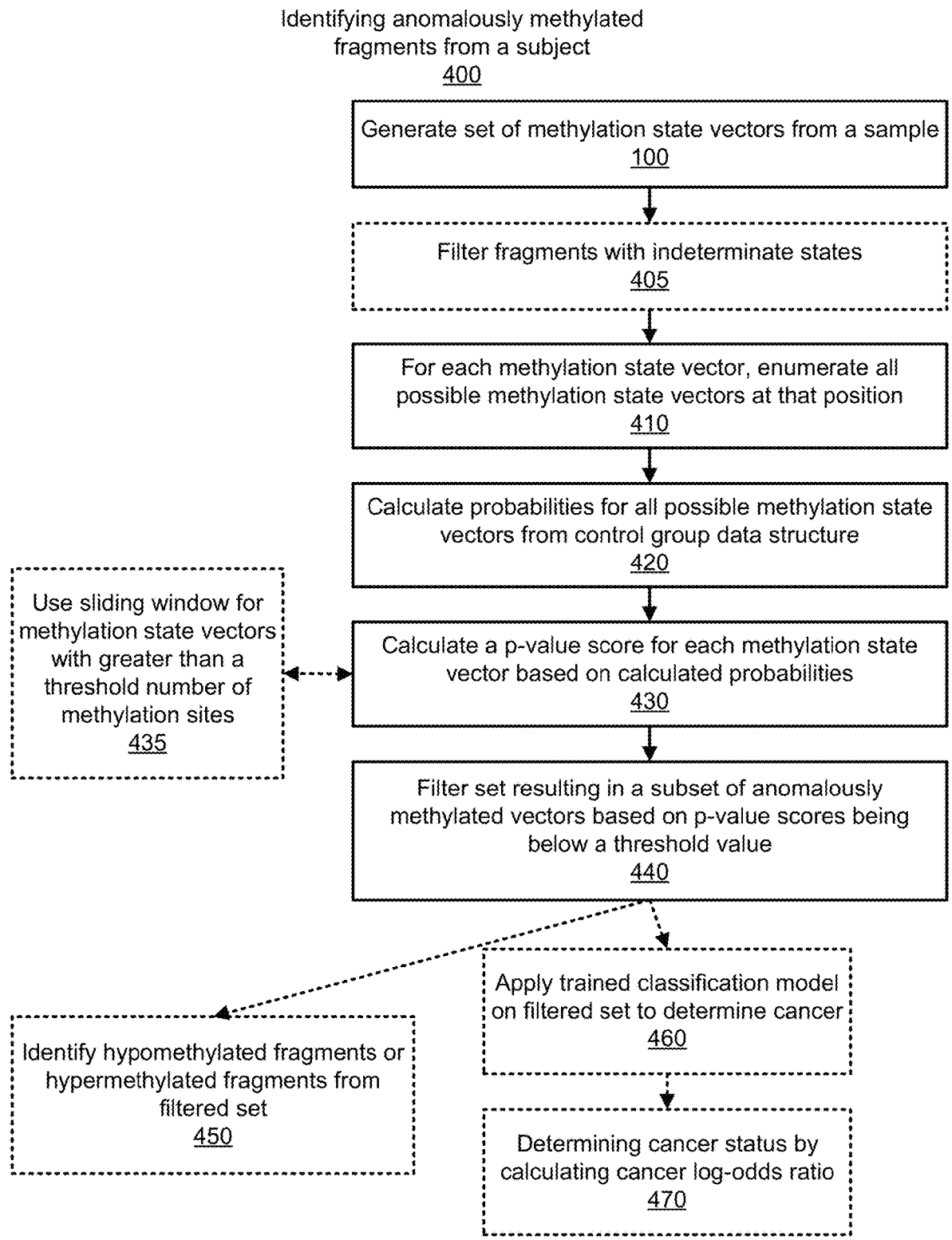
FIG. 4 is a flowchart describing a process for identifying anomalously methylated fragments from a subject, according to an embodiment.

FIG. 4 is a flowchart describing a process 400 for identifying anomalously methylated fragments from a subject, according to an embodiment. An example process 400 is visually illustrated in FIG. 5, and is further described below the description of FIG. 4. In process 400, the analytics system generates 100 methylation state vectors from cfDNA fragments of the subject. The analytics system handles each methylation state vector as follows.

In some embodiments, the analytics system filters 405 fragments having indeterminate states at one or more CpG sites. In such embodiments, the analytics system implements a prediction model to identify fragments not likely to have an anomalous methylation pattern for filtering. For a sample fragment, the prediction model calculates a sample probability that the sample fragment's methylation state vector occurs in comparison to the healthy control group data structure. The prediction model randomly samples a subset of possible methylation state vectors encompassing the CpG sites in the sample fragment's methylation state vector. The prediction model calculates a probability corresponding to each of the sampled possible methylation state vectors. Probability calculations for the fragment's methylation state vector and the sampled possible methylation state vectors can be calculated according to a Markov chain model as will be described below in Section IV. B. Example P-Value Score Calculation. The prediction model calculates a proportion of the sampled possible methylation state vectors corresponding to probabilities less than or equal to the sample probability. The prediction model generates an estimated p-value score for the fragment based on the calculated proportion. The prediction model may filter fragments corresponding to p-value scores above a threshold and retain fragments corresponding to p-value scores below the threshold.

In additional embodiments, the prediction model may calculate a confidence probability that is used by the prediction model to determine when to continue or when to terminate sampling. The confidence probability describes how likely the fragment's true p-value score (the calculation of the true p-value score further described below Section IV. B. Example P-Value Score Calculation) is below a threshold based on the estimated p-value score and the probabilities of the sampled possible methylation state vectors. The prediction model may sample additional one or more possible methylation state vectors while iteratively calculating the estimated p-value score and the confidence probability. The prediction model may then terminate the sampling when the confidence probability is above a confidence threshold.

For a given methylation state vector, the analytics system enumerates 410 all possibilities of methylation state vectors having the same starting CpG site and same length (i.e., set of CpG sites) in the methylation state vector. As each observed methylation state may be methylated or unmethylated there are only two possible states at each CpG site, and thus the count of distinct possibilities of methylation state vectors depends on a power of 2, such that a methylation state vector of length n would be associated with $2^n$ possibilities of methylation state vectors. With methylation state vectors inclusive of indeterminate states for one or more CpG sites, the analytics system may enumerate 410 possibilities of methylation state vectors considering only CpG sites that have observed states.

The analytics system calculates 420 the probability of observing each possibility of methylation state vector for the identified starting CpG site/methylation state vector length by accessing the healthy control group data structure. In one embodiment, calculating the probability of observing a given possibility uses a Markov chain probability to model the joint probability calculation which will be described in greater detail with respect to FIG. 5 below. In other embodiments, calculation methods other than Markov chain probabilities are used to determine the probability of observing each possibility of methylation state vector.

The analytics system calculates 430 a p-value score for the methylation state vector using the calculated probabilities for each possibility. In one embodiment, this includes identifying the calculated probability corresponding to the possibility that matches the methylation state vector in question. Specifically, this is the possibility having the same set of CpG sites, or similarly the same starting CpG site and length as the methylation state vector. The analytics system sums the calculated probabilities of any possibilities having probabilities less than or equal to the identified probability to generate the p-value score.

This p-value represents the probability of observing the methylation state vector of the fragment or other methylation state vectors even less probable in the healthy control group. A low p-value score, thereby, generally corresponds to a methylation state vector which is rare in a healthy subject, and which causes the fragment to be labeled anomalously methylated, relative to the healthy control group. A high p-value score generally relates to a methylation state vector is expected to be present, in a relative sense, in a healthy subject. If the healthy control group is a non-cancerous group, for example, a low p-value indicates that the fragment is anomalous methylated relative to the non-cancer group, and therefore possibly indicative of the presence of cancer in the test subject.

As above, the analytics system calculates p-value scores for each of a plurality of methylation state vectors, each representing a cfDNA fragment in the test sample. To identify which of the fragments are anomalously methylated, the analytics system may filter 440 the set of methylation state vectors based on their p-value scores. In one embodiment, filtering is performed by comparing the p-values scores against a threshold and keeping only those fragments below the threshold. This threshold p-value score could be on the order of 0.1, 0.01, 0.001, 0.0001, or similar.

According to example results from the process 400, the analytics system yields a median (range) of 2,800 (1,500-12,000) fragments with anomalous methylation patterns for participants without cancer in training, and a median (range) of 3,000 (1,200-220,000) fragments with anomalous methylation patterns for participants with cancer in training. These filtered sets of fragments with anomalous methylation patterns may be used for the downstream analyses as described below in Section IV.D. Example Use Cases for Filtered Sets of Anomalous Fragments.

IV.B. Example P-Value Score Calculation

FIG. 5 is an illustration 500 of an example p-value score calculation, according to an embodiment. To calculate a p-value score given a test methylation state vector 505, the analytics system takes that test methylation state vector 505 and enumerates 410 possibilities of methylation state vectors. In this illustrative example, the test methylation state vector 505 is <M23, M24, M25, U26>. As the length of the test methylation state vector 505 is 4, there are 2^4 possibilities of methylation state vectors encompassing CpG sites 23-26. In a generic example, the number of possibilities of methylation state vectors is 2^n, where n is the length of the test methylation state vector or alternatively the length of the sliding window (described further below).

The analytics system calculates 420 probabilities 515 for the enumerated possibilities of methylation state vectors. As methylation is conditionally dependent on methylation state of nearby CpG sites, one way to calculate the probability of observing a given methylation state vector possibility is to use Markov chain model. Generally a methylation state vector such as $<S_1, S_2, \ldots, S_n>$, where S denotes the methylation state whether methylated (denoted as M), unmethylated (denoted as U), or indeterminate (denoted as I), has a joint probability that can be expanded using the chain rule of probabilities as:

$$P(<S_1, S_2, \ldots, S_n>) = P(S_n|S_1, \ldots, S_{n-1}) * P(S_{n-1}|S_1, \ldots, S_{n-2}) * \ldots * P(S_2|S_1) * P(S_1) \quad (1)$$

Markov chain model can be used to make the calculation of the conditional probabilities of each possibility more efficiently. In one embodiment, the analytics system selects a Markov chain order k which corresponds to how many prior CpG sites in the vector (or window) to consider in the conditional probability calculation, such that the conditional probability is modeled as $P(S_n|S_1, \ldots, S_{n-1}) \sim P(S_n|S_{n-k-2}, \ldots, S_{n-1})$.

To calculate each Markov modeled probability for a possibility of methylation state vector, the analytics system accesses the control group's data structure, specifically the counts of various strings of CpG sites and states. To calculate $P(M_n|S_{n-k-2}, \ldots, S_{n-1})$, the analytics system takes a ratio of the stored count of the number of strings from the data structure matching $<S_{n-k-2}, \ldots, S_{n-1}, M_n>$ divided by the sum of the stored count of the number of strings from the data structure matching $<S_{n-k-2}, \ldots, S_{n-1}, M_n>$ and $<S_{n-k-2}, \ldots, S_{n-1}, U_n>$. Thus, $P(M_n|S_{n-k-2}, \ldots, S_{n-1})$, is calculated ratio having the form:

$$\frac{\# \text{ of } \langle S_{n-k-2}, \ldots, S_{n-1}, M_n \rangle}{\# \text{ of } \langle S_{n-k-2}, \ldots, S_{n-1}, M_n \rangle + \# \text{ of } \langle S_{n-k-2}, \ldots, S_{n-1}, U_n \rangle} \quad (2)$$

The calculation may additionally implement a smoothing of the counts by applying a prior distribution. In one embodiment, the prior distribution is a uniform prior as in Laplace smoothing. As an example of this, a constant is added to the numerator and another constant (e.g., twice the constant in the numerator) is added to the denominator of the above equation. In other embodiments, an algorithmic technique such as Knesser-Ney smoothing is used.

In the illustration, the above denoted formulas are applied to the test methylation state vector 505 covering sites 23-26. Once the calculated probabilities 515 are completed, the analytics system calculates 430 a p-value score 525 that sums the probabilities that are less than or equal to the probability of possibility of methylation state vector matching the test methylation state vector 505.

In embodiments with indeterminate states, the analytics system may calculate a p-value score summing out CpG sites with indeterminates states in a fragment's methylation state vector. The analytics system identifies all possibilities that have consensus with the all methylation states of the methylation state vector excluding the indeterminate states. The analytics system may assign the probability to the methylation state vector as a sum of the probabilities of the identified possibilities. As an example, the analytics system calculates a probability of a methylation state vector of $<M_1, I_2, U_3>$ as a sum of the probabilities for the possibilities of methylation state vectors of $<M_1, M_2, U_3>$ and $<M_1, U_2, U_3>$ since methylation states for CpG sites 1 and 3 are observed and in consensus with the fragment's methylation states at CpG sites 1 and 3. This method of summing out CpG sites with indeterminate states uses calculations of probabilities of possibilities up to $2^i$, wherein i denotes the number of indeterminate states in the methylation state vector. In additional embodiments, a dynamic programming algorithm may be implemented to calculate the probability of a methylation state vector with one or more indeterminate states. Advantageously, the dynamic programming algorithm operates in linear computational time.

In one embodiment, the computational burden of calculating probabilities and/or p-value scores may be further reduced by caching at least some calculations. For example, the analytic system may cache in transitory or persistent memory calculations of probabilities for possibilities of methylation state vectors (or windows thereof). If other fragments have the same CpG sites, caching the possibility probabilities allows for efficient calculation of p-score values without needing to re-calculate the underlying possibility probabilities. Equivalently, the analytics system may calculate p-value scores for each of the possibilities of methylation state vectors associated with a set of CpG sites from vector (or window thereof). The analytics system may cache the p-value scores for use in determining the p-value scores of other fragments including the same CpG sites. Generally, the p-value scores of possibilities of methylation state vectors having the same CpG sites may be used to determine the p-value score of a different one of the possibilities from the same set of CpG sites.

IV.C. Sliding Window

In one embodiment, the analytics system uses 435 a sliding window to determine possibilities of methylation state vectors and calculate p-values. Rather than enumerating possibilities and calculating p-values for entire methylation state vectors, the analytics system enumerates possibilities and calculates p-values for only a window of sequential CpG sites, where the window is shorter in length (of CpG sites) than at least some fragments (otherwise, the window would serve no purpose). The window length may be static, user determined, dynamic, or otherwise selected.

In calculating p-values for a methylation state vector larger than the window, the window identifies the sequential set of CpG sites from the vector within the window starting from the first CpG site in the vector. The analytic system calculates a p-value score for the window including the first CpG site. The analytics system then "slides" the window to the second CpG site in the vector, and calculates another p-value score for the second window. Thus, for a window size l and methylation vector length m, each methylation state vector will generate m−l+1 p-value scores. After completing the p-value calculations for each portion of the vector, the lowest p-value score from all sliding windows is taken as the overall p-value score for the methylation state vector. In another embodiment, the analytics system aggregates the p-value scores for the methylation state vectors to generate an overall p-value score.

Using the sliding window helps to reduce the number of enumerated possibilities of methylation state vectors and their corresponding probability calculations that would otherwise need to be performed. Example probability calculations are shown in FIG. 5, but generally the number of possibilities of methylation state vectors increases exponentially by a factor of 2 with the size of the methylation state vector. To give a realistic example, it is possible for fragments to have upwards of 54 CpG sites. Instead of computing probabilities for $2^{54}$ (~$1.8 \times 10^{16}$) possibilities to generate a single p-score, the analytics system can instead use a window of size 5 (for example) which results in 50 p-value calculations for each of the 50 windows of the methylation state vector for that fragment. Each of the 50 calculations enumerates $2^5$ (32) possibilities of methylation state vectors, which total results in $50 \times 2^5$ ($1.6 \cdot 10^3$) probability calculations. This results in a vast reduction of calculations to be performed, with no meaningful hit to the accurate identification of anomalous fragments. This additional step can also be applied when validating 240 the control group with the validation group's methylation state vectors.

IV.D. Example Use Cases for Filtered Sets of Anomalous Fragments

Figure 6:
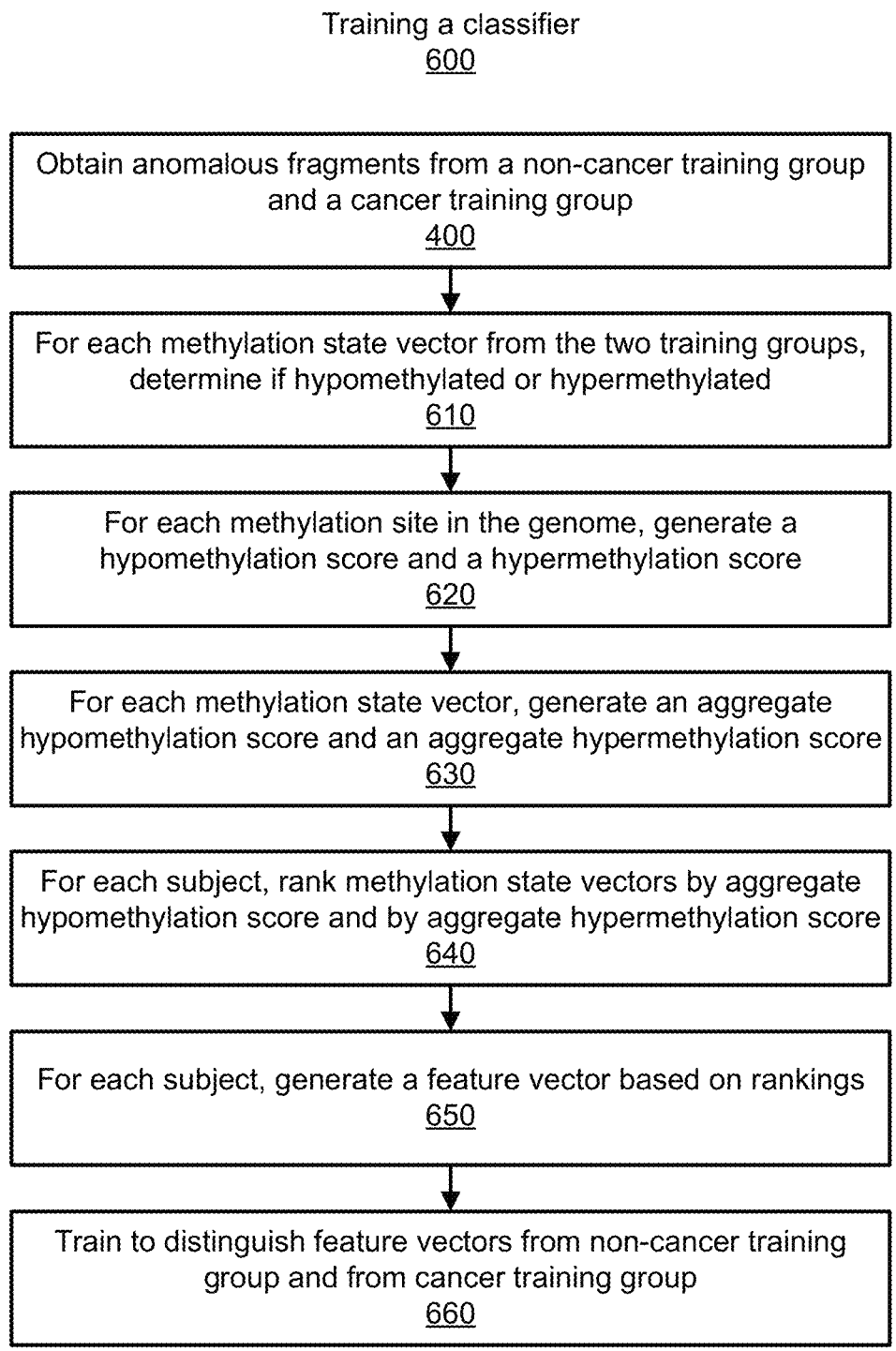
FIG. 6 is a flowchart describing a process of training a classifier based on methylation state of fragments, according to an embodiment.

The analytics system may perform any variety and/or possibility of additional analyses with the set of anomalous fragments. One additional analysis identifies 450 hypomethylated fragments or hypermethylated fragments from the filtered set. Fragments that are hypomethylated or hypermethylated may be defined as fragments of a certain length of CpG sites (e.g., more than 3, 4, 5, 6, 7, 8, 9, 10, etc.) with a high percentage of methylated CpG sites (e.g., more than 80%, 85%, 90%, or 95%, or any other percentage within the range of 50%-100%) or a high percentage of unmethylated CpG sites (e.g., more than 80%, 85%, 90%, or 95%, or any other percentage within the range of 50%-100%), respectively. FIG. 6, described below, illustrates an example process for identifying these hypomethylated or hypermethylated portions of a genome based on the set of anomalously methylated fragments.

An alternate analysis applies 460 a trained classification model on the set of anomalous fragments. The trained classification model can be trained to identify any condition of interest that can be identified from the methylation state vectors. In one embodiment, the trained classification model is a binary classifier trained based on methylation states for cfDNA fragments obtained from a subject cohort with cancer, and optionally based on methylation states for cfDNA fragments obtained from a healthy subject cohort without cancer, and is then used to classify a test subject probability of having cancer, or not having cancer, based on anomalously methylation state vectors. In further embodiments, different classifiers may be trained using subject cohorts known to have particular cancer (e.g., breast, lung, prostrate, etc.) to predict whether a test subject has those specific cancers.

In one embodiment, the classifier is trained based on information about hyper/hypo methylated regions from the process 450 and as described with respect to FIG. 6 below.

Another additional analysis calculates the log-odds ratio that the anomalous fragments from a subject are indicative of cancer generally, or of particular types of cancer. The log-odds ratio can be calculated by taking the log of a ratio of a probability of being cancerous over a probability of being non-cancerous (i.e., one minus the probability of being cancerous), both as determined by the applied 460 classification model.

Figure 7A:
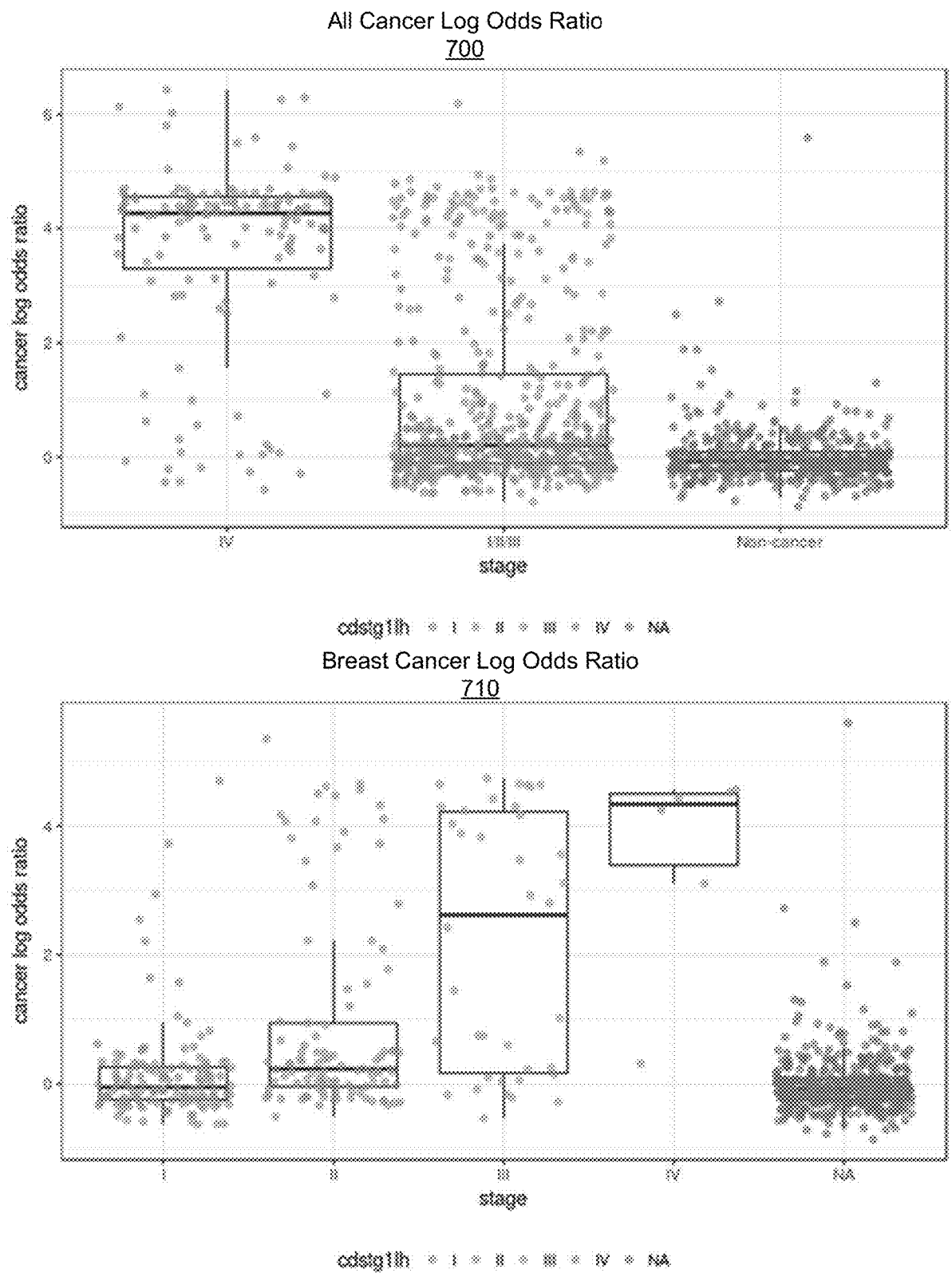
Figure 7C:
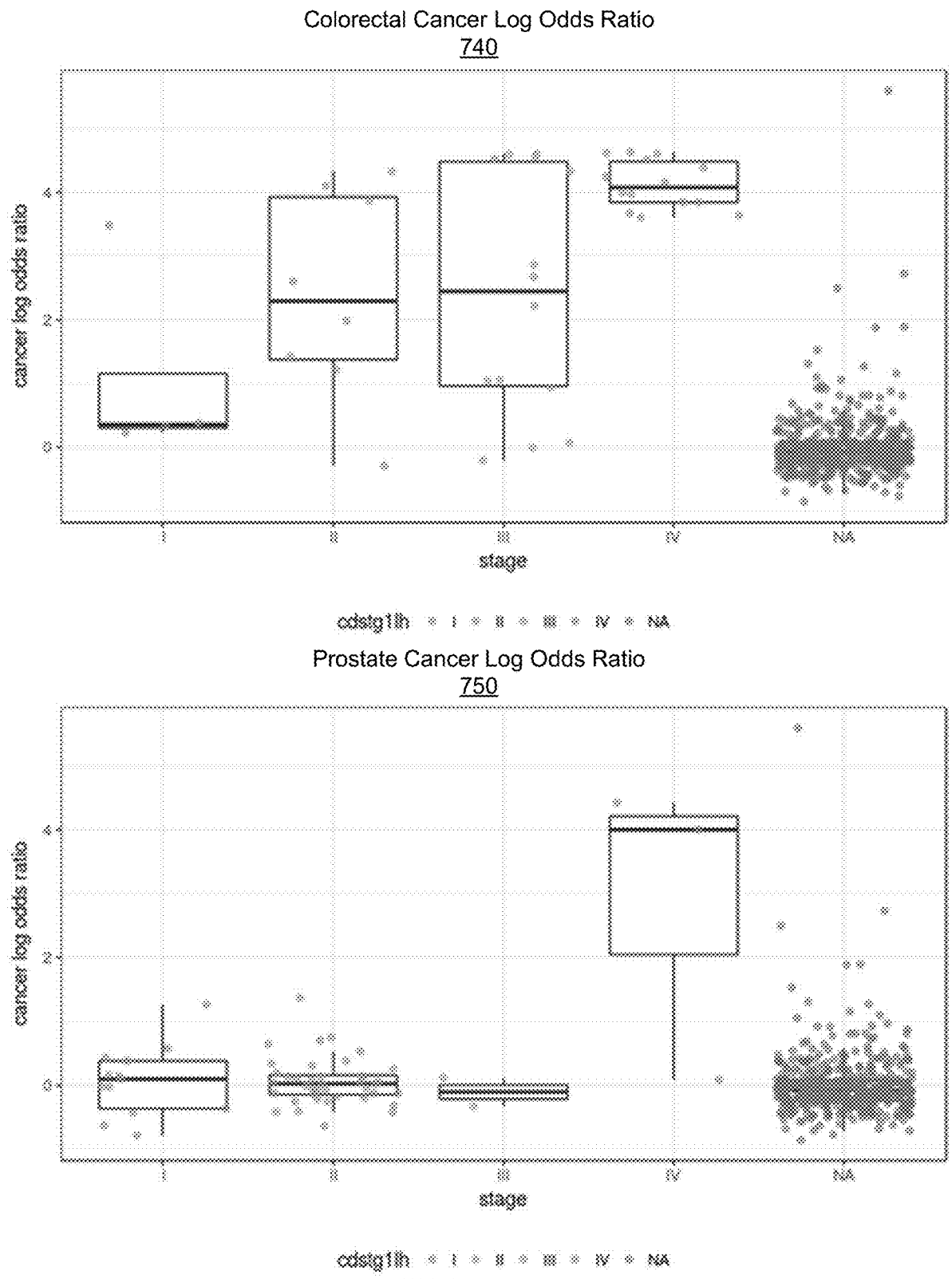

FIGS. 7A-7C show graphs of various cancers from various subjects across different stages, plotting the log-odds ratio of the anomalous fragments identified according to the process described with respect to FIG. 4 above. This data was obtained through testing of more than 1700 clinically evaluable subjects with over 1400 subjects filtered including nearly 600 subjects without cancer and just over 800 subjects with cancer. The first graph 700 in FIG. 7A shows all cancer cases across three different levels—non-cancer; stage I/II/II; and stage IV. The cancer log-odds ratio for stage IV is significantly larger than those for stage I/II/II and non-cancer. The second graph 710 in FIG. 7A shows breast cancer cases across all stages of cancer and non-cancer, with a similar progression in log-odds ratio increasing through the progressive stages of cancer. The third graph 720 in FIG. 7B shows breast cancer sub-types. Noticeably sub-types HER2+ and TNBC are more spread out, whereas HR+/HER2− is concentrated closer to ~1. The fourth graph 730 in FIG. 7C shows lung cancer cases across all stages of cancer and non-cancer with steady progression through progressive stages of the lung cancer. The fifth graph 740 shows colorectal cancer cases across all stages of cancer and non-cancer, again showing steady progression through progressive stages of the colorectal cancer. The sixth graph 750 in FIG. 7C shows prostate cancer cases across all stages of cancer and non-cancer. This example is different than most of the previously illustrated, only stage IV is significantly different compared to other stages I/II/II and non-cancer.

V. Hyper/Hypo Methylated Regions and a Classifier

FIG. 6 is a flowchart describing a process 600 of training a classifier based on methylation state of cfDNA fragments, according to an embodiment. An analytics system may be used to perform the process 600. The process accesses two training groups of samples—a non-cancer group and a cancer group—and obtains 400 a non-cancer set of methylation state vectors and a cancer set of methylation state vectors comprising the anomalous fragments of the samples in each group. The anomalous fragments may be identified according to the process 400 of FIG. 4, for example.

The analytics system determines 610, for each methylation state vector, whether the methylation state vector is hypomethylated or hypermethylated. Here, the hypermethylated or hypomethylated label is assigned if at least some number of CpG sites have a particular state (methylated or unmethylated, respectively) and/or have a threshold percentage of sites that are the particular state (again, methylated or unmethylated, respectively). As defined above, cfDNA fragments are identified as hypomethylated or hypermethylated, respectively, if the fragment has at least five CpG sites that are either unmethylated or methylated and (logical AND) above 80% of the fragments CpG sites being unmethylated or methylated.

In an alternate embodiment, the analytics system considers portions of the methylation state vector and determines whether the portion is hypomethylated or hypermethylated, and may distinguish that portion to be hypomethylated or hypermethylated. This alternative resolves missing methylation state vectors which are large in size but contain at least one region of dense hypomethylation or hypermethylation. This process of defining hypomethylation and hypermethylation can be applied in step 450 of FIG. 4.

The analytics system generates 620 a hypomethylation score and a hypermethylation score per CpG site in the genome. To generate either score at a given CpG site, the classifier takes four counts at that CpG site—(1) count of (methylations state) vectors of the cancer set labeled hypomethylated that overlap the CpG site; (2) count of vectors of the cancer set labeled hypermethylated that overlap the CpG site; (3) count of vectors of the non-cancer set labeled hypomethylated that overlap the CpG site; and (4) count of vectors of the non-cancer set labeled hypermethylated that overlap the CpG site. Additionally the process may normalize these counts for each group to account for variance in group size between the non-cancer group and the cancer group.

In one embodiment, the hypomethylation score at a given CpG site is defined as log of a ratio of (1) over (3). Similarly the hypermethylation score is calculated as log of a ratio of (2) over (4). Additionally these ratios may be calculated with an additional smoothing technique as discussed above.

In another embodiment, the hypomethylation score is defined as a ratio of (1) over (1) summed with (3). The hypermethylation score is defined as a ratio of (2) over (2) summed with (4). Similar to the embodiment above, smoothing techniques may be implemented into the ratios.

The analytics system generates 630 an aggregate hypomethylation score and an aggregate hypermethylation score for each anomalous methylation state vector. The aggregate hyper and hypo methylation scores, are determined based on the hyper and hypo methylation scores of the CpG sites in the methylation state vector. In one embodiment, the aggregate hyper and hypo methylation scores are assigned as the largest hyper and hypo methylation scores of the sites in each state vector, respectively. However, in alternate embodiments, the aggregate scores could be based on means, medians, or other calculations that use the hyper/hypo methylation scores of the sites in each vector. In one embodiment, the analytics system assigns the greater of the aggregate hypomethylation score and the aggregate hypermethylation score to the anomalous methylation state vector.

The analytics system then ranks 640 all of that subject's methylation state vectors by their aggregate hypomethylation score and by their aggregate hypermethylation score, resulting in two rankings per subject. The process selects aggregate hypomethylation scores from the hypomethylation ranking and aggregate hypermethylation scores from the hypermethylation ranking. With the selected scores, the classifier generates 650 a single feature vector for each subject. In one embodiment, the scores selected from either ranking are selected with a fixed order that is the same the for each generated feature vector for each subject in each of the training groups. As an example, in one embodiment the classifier selects the first, the second, the fourth, the eighth, the sixteenth, the thirty-second, the sixty-fourth aggregate hyper methylation score, and similarly for each aggregate hypo methylation score, from each ranking and writes those scores in the feature vector for that subject (totaling 14 features in the feature vector). In additional embodiments, to adjust for sample sequencing depth, the analytics system adjusts ranks in linear proportion to relative sample depth. For example, if the relative sample depth was x, interpolated scores were taken at x*the original ranks (i.e. x=1.1, we take scores computed at ranks 1.1, 2.2, . . . , x*2i). The analytics system may then define the feature vector based on the adjusted ranks to be used in further classification.

The analytics system trains 660 a binary classifier to distinguish feature vectors between the cancer and non-cancer training groups. The analytics system may group the training samples into sets of one or more training samples for iterative batch training of the binary classifier. After inputting all sets of training samples including their training feature vectors and adjusting the classification parameters, the binary classifier is sufficiently trained to label test samples according to their feature vector within some margin of error. For example, in one embodiment, the classifier determines a likelihood or probability score (e.g., from 0 to 100) that the sample feature vector is from a subject with cancer. In some embodiments, the probability score is compared to a threshold probability to determine whether or not the subject has cancer. In other embodiments, a probability score of greater than or equal to 60 indicated that the subject has cancer. In still other embodiments, a probability score greater than or equal to 65, greater than or equal to 70, greater than or equal to 75, greater than or equal to 80, greater than or equal to 85, greater than or equal to 90, or greater than or equal to 95, indicated that the subject has cancer. Generally, any one of a number of classification techniques may be used. These techniques are numerous including potential use of kernel methods, machine learning algorithms such as multilayer neural networks, etc.

In one embodiment, the classifier is a non-linear classifier. In a specific embodiment, the classifier is a non-linear classifier utilizing a L2-regularized kernel logistic regression with a Gaussian radial basis function (RBF) kernel. Specifically, a regularized kernel logistic regression classifier (KLR) was trained using the isotropic radial basis function (power exponential 2) as the kernel with scale parameter gamma and L2 regularization parameter lambda. Gamma and lambda were optimized for holdout log-loss using internal cross-validation within specified training data, and were optimized using grid-search in multiplicative steps, starting at the maximum value and halving the parameter each step. In other embodiments, the classifier can include other types of classifiers, such as a random forest classifier, a mixture model, a convolutional neural network, or an autoencoder model.

VI. Example Sequencer and Analytics System

Figure 8A:
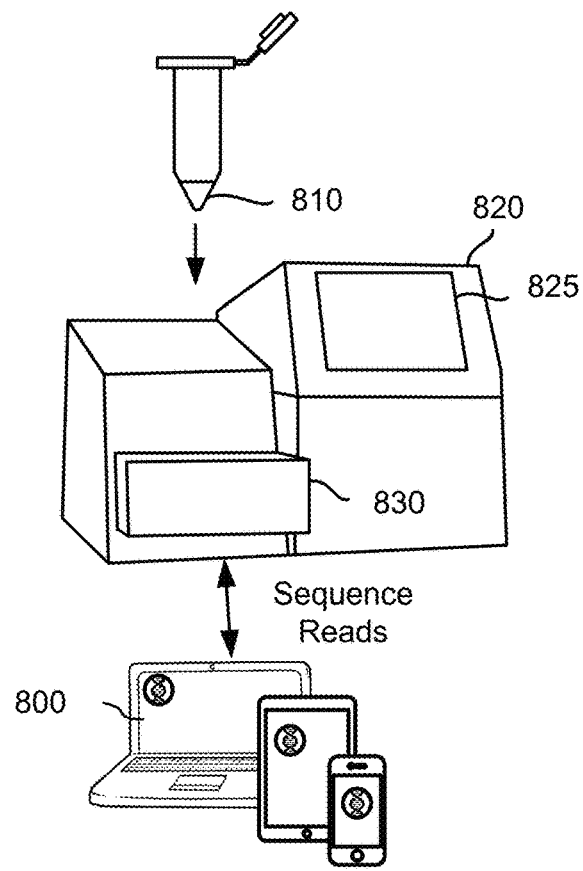
FIG. 8A is a flowchart of devices for sequencing nucleic acid samples according to one embodiment.

FIG. 8A is a flowchart of devices for sequencing nucleic acid samples according to one embodiment. This illustrative flowchart includes devices such as a sequencer 820 and an analytics system 800. The sequencer 820 and the analytics system 800 may work in tandem to perform one or more steps in the processes 100 of FIG. 1A, 200 of FIG. 2, 240 of FIG. 3, 400 of FIG. 4, 600 of FIG. 6, and other process described herein.

In various embodiments, the sequencer 820 receives an enriched nucleic acid sample 810. As shown in FIG. 8A, the sequencer 820 can include a graphical user interface 825 that enables user interactions with particular tasks (e.g., initiate sequencing or terminate sequencing) as well as one more loading stations 830 for loading a sequencing cartridge including the enriched fragment samples and/or for loading necessary buffers for performing the sequencing assays. Therefore, once a user of the sequencer 820 has provided the necessary reagents and sequencing cartridge to the loading station 830 of the sequencer 820, the user can initiate sequencing by interacting with the graphical user interface 825 of the sequencer 820. Once initiated, the sequencer 820 performs the sequencing and outputs the sequence reads of the enriched fragments from the nucleic acid sample 810.

In some embodiments, the sequencer 820 is communicatively coupled with the analytics system 800. The analytics system 800 includes some number of computing devices used for processing the sequence reads for various applications such as assessing methylation status at one or more CpG sites, variant calling or quality control. The sequencer 820 may provide the sequence reads in a BAM file format to the analytics system 800. The analytics system 800 can be communicatively coupled to the sequencer 820 through a wireless, wired, or a combination of wireless and wired communication technologies. Generally, the analytics system 800 is configured with a processor and non-transitory computer-readable storage medium storing computer instructions that, when executed by the processor, cause the processor to process the sequence reads or to perform one or more steps of any of the methods or processes disclosed herein.

In some embodiments, the sequence reads may be aligned to a reference genome using known methods in the art to determine alignment position information, e.g., part of step 140 of the process 100 in FIG. 1A. Alignment position may generally describe a beginning position and an end position of a region in the reference genome that corresponds to a beginning nucleotide based and an end nucleotide base of a given sequence read. Corresponding to methylation sequencing, the alignment position information may be generalized to indicate a first CpG site and a last CpG site included in the sequence read according to the alignment to the reference genome. The alignment position information may further indicate methylation statuses and locations of all CpG sites in a given sequence read. A region in the reference genome may be associated with a gene or a segment of a gene; as such, the analytics system 800 may label a sequence read with one or more genes that align to the sequence read. In one embodiment, fragment length (or size) is be determined from the beginning and end positions.

In various embodiments, for example when a paired-end sequencing process is used, a sequence read is comprised of a read pair denoted as R_1 and R_2. For example, the first read R_1 may be sequenced from a first end of a double-stranded DNA (dsDNA) molecule whereas the second read R_2 may be sequenced from the second end of the double-stranded DNA (dsDNA). Therefore, nucleotide base pairs of the first read R_1 and second read R_2 may be aligned consistently (e.g., in opposite orientations) with nucleotide bases of the reference genome. Alignment position information derived from the read pair R_1 and R_2 may include a beginning position in the reference genome that corresponds to an end of a first read (e.g., R_1) and an end position in the reference genome that corresponds to an end of a second read (e.g., R_2). In other words, the beginning position and end position in the reference genome represent the likely location within the reference genome to which the nucleic acid fragment corresponds. An output file having SAM (sequence alignment map) format or BAM (binary) format may be generated and output for further analysis.

Figure 8B:
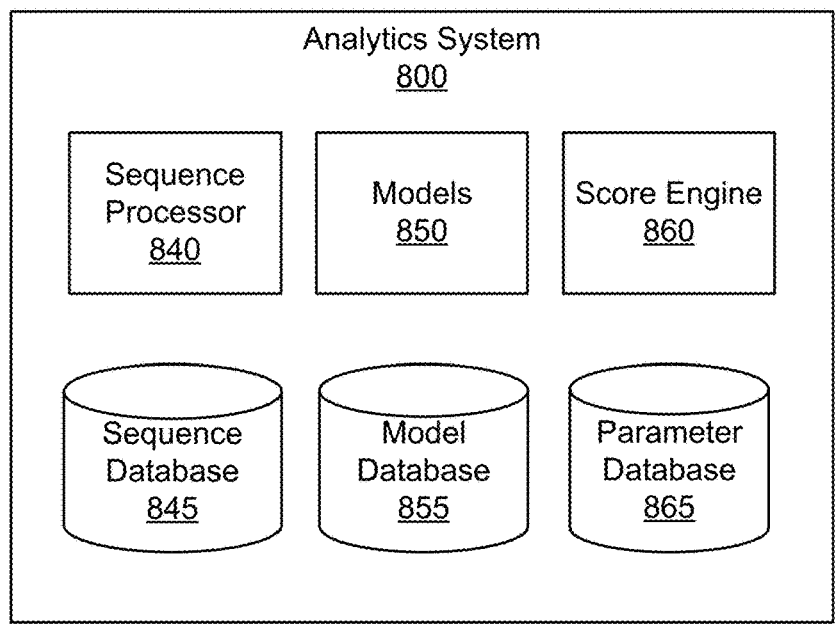
FIG. 8B provides an analytic system that analyzes methylation status of cfDNA according to one embodiment.

Referring now to FIG. 8B, FIG. 8B is a block diagram of an analytics system 800 for processing DNA samples according to one embodiment. The analytics system implements one or more computing devices for use in analyzing DNA samples. The analytics system 800 includes a sequence processor 840, sequence database 845, model database 855, models 850, parameter database 865, and score engine 860. In some embodiments, the analytics system 800 performs one or more steps in the processes 100 of FIG. 1A, 200 of FIG. 2, 240 of FIG. 3, 400 of FIG. 4, 600 of FIG. 6, and other process described herein.

The sequence processor 840 generates methylation state vectors for fragments from a sample. At each CpG site on a fragment, the sequence processor 840 generates a methylation state vector for each fragment specifying a location of the fragment in the reference genome, a number of CpG sites in the fragment, and the methylation state of each CpG site in the fragment whether methylated, unmethylated, or indeterminate via the process 100 of FIG. 1A. The sequence processor 840 may store methylation state vectors for fragments in the sequence database 845. Data in the sequence database 845 may be organized such that the methylation state vectors from a sample are associated to one another.

Further, multiple different models 850 may be stored in the model database 855 or retrieved for use with test samples. In one example, a model is a trained cancer classifier for determining a cancer prediction for a test sample using a feature vector derived from anomalous fragments. The training and use of the cancer classifier will be further discussed in conjunction with Section V. Hyper/Hypo Methylated Regions and a Classifier. The analytics system 800 may train the one or more models 850 and store various trained parameters in the parameter database 865. The analytics system 800 stores the models 850 along with functions in the model database 855.

During inference, the score engine 860 uses the one or more models 850 to return outputs. The score engine 860 accesses the models 850 in the model database 855 along with trained parameters from the parameter database 865. According to each model, the score engine receives an appropriate input for the model and calculates an output based on the received input, the parameters, and a function of each model relating the input and the output. In some use cases, the score engine 860 further calculates metrics correlating to a confidence in the calculated outputs from the model. In other use cases, the score engine 860 calculates other intermediary values for use in the model.

VII. Applications

In some embodiments, the methods, analytic systems and/or classifier of the present invention can be used to detect the presence of cancer, monitor cancer progression or recurrence, monitor therapeutic response or effectiveness, determine a presence or monitor minimum residual disease (MRD), or any combination thereof. For example, as described herein, a classifier can be used to generate a likelihood or probability score (e.g., from 0 to 100) that a sample feature vector is from a subject with cancer. In some embodiments, the probability score is compared to a threshold probability to determine whether or not the subject has cancer. In other embodiments, the likelihood or probability score can be assessed at different time points (e.g., before or after treatment) to monitor disease progression or to monitor treatment effectiveness (e.g., therapeutic efficacy). In still other embodiments, the likelihood or probability score can be used to make or influence a clinical decision (e.g., diagnosis of cancer, treatment selection, assessment of treatment effectiveness, etc.). For example, in one embodiment, if the likelihood or probability score exceeds a threshold, a physician can prescribe an appropriate treatment.

VII.A. Early Detection of Cancer

In some embodiments, the methods and/or classifier of the present invention are used to detect the presence or absence of cancer in a subject suspected of having cancer. For example, a classifier (as described herein) can be used to determine a likelihood or probability score that a sample feature vector is from a subject that has cancer.

In one embodiment, a probability score of greater than or equal to 60 can indicated that the subject has cancer. In still other embodiments, a probability score greater than or equal to 65, greater than or equal to 70, greater than or equal to 75, greater than or equal to 80, greater than or equal to 85, greater than or equal to 90, or greater than or equal to 95, indicated that the subject has cancer. In other embodiments, a probability score can indicate the severity of disease. For example, a probability score of 80 may indicate a more severe form, or later stage, of cancer compared to a score below 80 (e.g., a score of 70). Similarly, an increase in the probability score over time (e.g., at a second, later time point) can indicate disease progression or a decrease in the probability score over time (e.g., at a second, later time point) can indicate successful treatment.

In another embodiment, a cancer log-odds ratio can be calculated for a test subject by taking the log of a ratio of a probability of being cancerous over a probability of being non-cancerous (i.e., one minus the probability of being cancerous), as described herein. In accordance with this embodiment, a cancer log-odds ratio greater than 1 can indicated that the subject has cancer. In still other embodiments, a cancer log-odds ratio greater than 1.2, greater than 1.3, greater than 1.4, greater than 1.5, greater than 1.7, greater than 2, greater than 2.5, greater than 3, greater than 3.5, or greater than 4, indicated that the subject has cancer. In other embodiments, a cancer log-odds ratio can indicate the severity of disease. For example, a cancer log-odds ratio greater than 2 may indicate a more severe form, or later stage, of cancer compared to a score below 2 (e.g., a score of 1). Similarly, an increase in the cancer log-odds ratio over time (e.g., at a second, later time point) can indicate disease progression or a decrease in the cancer log-odds ratio over time (e.g., at a second, later time point) can indicate successful treatment.

According to aspects of the invention, the methods and systems of the present invention can be trained to detect or classify multiple cancer indications. For example, the methods, systems and classifiers of the present invention can be used to detect the presence of one or more, two or more, three or more, five or more, ten or more, fifteen or more, or twenty or more different types of cancer.

Examples of cancers that can be detected using the methods, systems and classifiers of the present invention include carcinoma, lymphoma, blastoma, sarcoma, and leukemia or lymphoid malignancies. More particular examples of such cancers include, but are not limited to, squamous cell cancer (e.g., epithelial squamous cell cancer), skin carcinoma, melanoma, lung cancer, including small-cell lung cancer, non-small cell lung cancer ("NSCLC"), adenocarcinoma of the lung and squamous carcinoma of the lung, cancer of the peritoneum, gastric or stomach cancer including gastrointestinal cancer, pancreatic cancer (e.g., pancreatic ductal adenocarcinoma), cervical cancer, ovarian cancer (e.g., high grade serous ovarian carcinoma), liver cancer (e.g., hepatocellular carcinoma (HCC)), hepatoma, hepatic carcinoma, bladder cancer (e.g., urothelial bladder cancer), testicular (germ cell tumor) cancer, breast cancer (e.g., HER2 positive, HER2 negative, and triple negative breast cancer), brain cancer (e.g., astrocytoma, glioma (e.g., glioblastoma)), colon cancer, rectal cancer, colorectal cancer, endometrial or uterine carcinoma, salivary gland carcinoma, kidney or renal cancer (e.g., renal cell carcinoma, nephroblastoma or Wilms' tumor), prostate cancer, vulval cancer, thyroid cancer, anal carcinoma, penile carcinoma, head and neck cancer, esophageal carcinoma, and nasopharyngeal carcinoma (NPC). Additional examples of cancers include, without limitation, retinoblastoma, thecoma, arrhenoblastoma, hematologic malignancies, including but not limited to non-Hodgkin's lymphoma (NHL), multiple myeloma and acute hematologic malignancies, endometriosis, fibrosarcoma, choriocarcinoma, laryngeal carcinomas, Kaposi's sarcoma, Schwannoma, oligodendroglioma, neuroblastomas, rhabdomyosarcoma, osteogenic sarcoma, leiomyosarcoma, and urinary tract carcinomas.

In some embodiments, the cancer is one or more of anorectal cancer, bladder cancer, breast cancer, cervical cancer, colorectal cancer, esophageal cancer, gastric cancer, head & neck cancer, hepatobiliary cancer, leukemia, lung cancer, lymphoma, melanoma, multiple myeloma, ovarian cancer, pancreatic cancer, prostate cancer, renal cancer, thyroid cancer, uterine cancer, or any combination thereof.

In some embodiments, the one or more cancer can be a "high-signal" cancer (defined as cancers with greater than 50% 5-year cancer-specific mortality), such as anorectal, colorectal, esophageal, head & neck, hepatobiliary, lung, ovarian, and pancreatic cancers, as well as lymphoma and multiple myeloma. High-signal cancers tend to be more aggressive and typically have an above-average cell-free nucleic acid concentration in test samples obtained from a patient.

VII.B. Cancer and Treatment Monitoring

In some embodiments, the likelihood or probability score can be assessed at different time points (e.g., or before or after treatment) to monitor disease progression or to monitor treatment effectiveness (e.g., therapeutic efficacy). For example, the present invention include methods that involve obtaining a first sample (e.g., a first plasma cfDNA sample) from a cancer patient at a first time point, determining a first likelihood or probability score therefrom (as described herein), obtaining a second test sample (e.g., a second plasma cfDNA sample) from the cancer patient at a second time point, and determine a second likelihood or probability score therefrom (as described herein).

In certain embodiments, the first time point is before a cancer treatment (e.g., before a resection surgery or a therapeutic intervention), and the second time point is after a cancer treatment (e.g., after a resection surgery or therapeutic intervention), and the method utilized to monitor the effectiveness of the treatment. For example, if the second likelihood or probability score decreases compared to the first likelihood or probability score, then the treatment is considered to have been successful. However, if the second likelihood or probability score increases compared to the first likelihood or probability score, then the treatment is considered to have not been successful. In other embodiments, both the first and second time points are before a cancer treatment (e.g., before a resection surgery or a therapeutic intervention). In still other embodiments, both the first and the second time points are after a cancer treatment (e.g., before a resection surgery or a therapeutic intervention) and the method used to monitor the effectiveness of the treatment or loss of effectiveness of the treatment. In still other embodiments, cfDNA samples may be obtained from a cancer patient at a first and second time point and analyzed. e.g., to monitor cancer progression, to determine if a cancer is in remission (e.g., after treatment), to monitor or detect residual disease or recurrence of disease, or to monitor treatment (e.g., therapeutic) efficacy.

Those of skill in the art will readily appreciate that test samples can be obtained from a cancer patient over any desired set of time points and analyzed in accordance with the methods of the invention to monitor a cancer state in the patient. In some embodiments, the first and second time points are separated by an amount of time that ranges from about 15 minutes up to about 30 years, such as about 30 minutes, such as about 1, 2, 3, 4, 5, 6, 7, 8, 9, 10, 11, 12, 13, 14, 15, 16, 17, 18, 19, 20, 21, 22, 23, or about 24 hours, such as about 1, 2, 3, 4, 5, 10, 15, 20, 25 or about 30 days, or such as about 1, 2, 3, 4, 5, 6, 7, 8, 9, 10, 11, or 12 months, or such as about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5 or about 30 years. In other embodiments, test samples can be obtained from the patient at least once every 3 months, at least once every 6 months, at least once a year, at least once every 2 years, at least once every 3 years, at least once every 4 years, or at least once every 5 years.

VII.C. Treatment

In still another embodiment, the likelihood or probability score can be used to make or influence a clinical decision (e.g., diagnosis of cancer, treatment selection, assessment of treatment effectiveness, etc.). For example, in one embodiment, if the likelihood or probability score exceeds a threshold, a physician can prescribe an appropriate treatment (e.g., a resection surgery, radiation therapy, chemotherapy, and/or immunotherapy).

A classifier (as described herein) can be used to determine a likelihood or probability score that a sample feature vector is from a subject that has cancer. In one embodiment, an appropriate treatment (e.g., resection surgery or therapeutic) is prescribed when the likelihood or threshold exceeds a threshold. For example, in one embodiment, if the likelihood or probability score is greater than or equal to 60 one or more appropriate treatments are prescribed. In another embodiments, if the likelihood or probability score is greater than or equal to 65, greater than or equal to 70, greater than or equal to 75, greater than or equal to 80, greater than or equal to 85, greater than or equal to 90, or greater than or equal to 95, one or more appropriate treatments are prescribed. In other embodiments, a cancer log-odds ratio can indicate the effectiveness of a cancer treatment. For example, an increase in the cancer log-odds ratio over time (e.g., at a second, after treatment) can indicate that the treatment was not effective. Similarly, a decrease in the cancer log-odds ratio over time (e.g., at a second, after treatment) can indicate successful treatment. In another embodiment, if the cancer log-odds ratio is greater than 1, greater than 1.5, greater than 2, greater than 2.5, greater than 3, greater than 3.5, or greater than 4, one or more appropriate treatments are prescribed.

In some embodiments, the treatment is one or more cancer therapeutic agents selected from the group consisting of a chemotherapy agent, a targeted cancer therapy agent, a differentiating therapy agent, a hormone therapy agent, and an immunotherapy agent. For example, the treatment can be one or more chemotherapy agents selected from the group consisting of alkylating agents, antimetabolites, anthracyclines, anti-tumor antibiotics, cytoskeletal disruptors (taxans), topoisomerase inhibitors, mitotic inhibitors, corticosteroids, kinase inhibitors, nucleotide analogs, platinum-based agents and any combination thereof. In some embodiments, the treatment is one or more targeted cancer therapy agents selected from the group consisting of signal transduction inhibitors (e.g. tyrosine kinase and growth factor receptor inhibitors), histone deacetylase (HDAC) inhibitors, retinoic receptor agonists, proteosome inhibitors, angiogenesis inhibitors, and monoclonal antibody conjugates. In some embodiments, the treatment is one or more differentiating therapy agents including retinoids, such as tretinoin, alitretinoin and bexarotene. In some embodiments, the treatment is one or more hormone therapy agents selected from the group consisting of anti-estrogens, aromatase inhibitors, progestins, estrogens, anti-androgens, and GnRH agonists or analogs. In one embodiment, the treatment is one or more immunotherapy agents selected from the group comprising monoclonal antibody therapies such as rituximab (RITUXAN) and alemtuzumab (CAMPATH), non-specific immunotherapies and adjuvants, such as BCG, interleukin-2 (IL-2), and interferon-alfa, immunomodulating drugs, for instance, thalidomide and lenalidomide (REVLIMID). It is within the capabilities of a skilled physician or oncologist to select an appropriate cancer therapeutic agent based on characteristics such as the type of tumor, cancer stage, previous exposure to cancer treatment or therapeutic agent, and other characteristics of the cancer.

VIII. Example

VIII.A. Use of Method of Detecting Anomalous Methylated Fragments for Diagnosis of Cancer Study design and samples: CCGA (NCT02889978) is a prospective, multi-center, case-control, observational study with longitudinal follow-up. De-identified biospecimens were collected from approximately 15,000 participants from 142 sites. Samples were divided into training (1,785) and test (1,015) sets; samples were selected to ensure a prespecified distribution of cancer types and non-cancers across sites in each cohort, and cancer and non-cancer samples were frequency age-matched by gender.

Whole-genome bisulfite sequencing: Cf DNA was isolated from plasma, and whole-genome bisulfite sequencing (WGBS; 30× depth) was employed for analysis of cfDNA. CfDNA was extracted from two tubes of plasma (up to a combined volume of 10 ml) per patient using a modified QIAamp Circulating Nucleic Acid kit (Qiagen; Germantown, MD). Up to 75 ng of plasma cfDNA was subjected to bisulfite conversion using the EZ-96 DNA Methylation Kit (Zymo Research, D5003). Converted cfDNA was used to prepare dual indexed sequencing libraries using Accel-NGS Methyl-Seq DNA library preparation kits (Swift BioSciences; Ann Arbor, MI) and constructed libraries were quantified using KAPA Library Quantification Kit for Illumina Platforms (Kapa Biosystems; Wilmington, MA). Four libraries along with 10% PhiX v3 library (Illumina, FC-110-3001) were pooled and clustered on an Illumina NovaSeq 6000 S2 flow cell followed by 150-bp paired-end sequencing (30×).

Analysis of cfDNA and classification of cancer versus non-cancer: For each sample, the WGBS fragment set was reduced to a small subset of fragments having an anomalous methylation pattern. Additionally, hyper or hypomethylated cfDNA fragments were selected. cfDNA fragments selected for having an anomalous methylation pattern and being hyper or hypermethylated are referred to as "unusual fragments of extreme methylation status" or "UFXM", herein. Fragments occurring at high frequency in individuals without cancer, or that have unstable methylation, are unlikely to produce highly discriminatory features for classification of cancer status. We therefore produced a statistical model and a data structure of typical fragments using an independent reference set of 108 non-smoking participants without cancer (age: 58±14 years, 79 [73%] women) (i.e., a reference genome) from the CCGA study. These samples were used to train a markov-chain model (order 3) estimating the likelihood of a given sequence of CpG methylation statuses within a fragment as further described above in IV. B. This model was demonstrated to be calibrated within the normal fragment range (p-value>0.001) and was used to reject fragments with a p-value from the markov model as >=0.001 as insufficiently unusual.

As described above, further data reduction step selected only fragments with at least 5 CpGs covered, and average methylation either >0.9 (hyper methylated) or <0.1 (hypomethylated). This procedure resulted in a median (range) of 2,800 (1,500-12,000) UFXM fragments for participants without cancer in training, and a median (range) of 3,000 (1,200-220,000) UFXM fragments for participants with cancer in training. As this data reduction procedure only used reference set data, this stage was only required to be applied to each sample once.

At selected loci within the genome, an approximate log-ratio score for informativeness for cancer status was constructed separately for both hyper- and hypo-methylated UFXM. First, for each sample at the locus a binary feature was generated: 0 if no UFXM fragment overlapped that locus within that sample, 1 if there existed a UFXM fragment overlapping the locus. The number of positive values (1s) in samples were then counted from participants with (C_c) and without cancer (C_nc). The log-ratio score was then constructed as: $\log(C\_c+1)-\log(C\_nc+1)$, adding a regularization term to the counts, and discarding the normalization term relating to the total number of samples within each group as it is constant ($\log[N\_nc+2]-\log[N\_c+2]$). Scores were constructed at the locations of all CpG sites within the genome, resulting in approximately 25M loci with assigned scores: one score for UFXM hypermethylated fragments and one score for UFXM hypo-methylated fragments.

Given a locus-specific log-ratio score, UFXM fragments in a sample were scored by taking the maximum of all log-ratio scores for loci within the fragment and matching the methylation category of either hyper- or hypo-methylated. This resulted in one score per UFXM fragment within a sample.

This fragment-level scores within a sample were reduced to a small set of features per sample by taking the scores of a subset of extreme-ranked fragments within each sample, separately for both hyper- and hypo-methylated fragments. In this way, information for the most informative fragments in each sample was captured using a small set of useful features. In a low cfDNA tumor fraction sample, only a minority of fragments were expected to be unusually informative.

In each category of fragments, the rank 1,2,4 . . . 64 ($2^i$, i in 0:6) largest scores were selected for fragments within each category of hyper- and hypo-methylated UFXM, resulting in 14 features (7 and 7). To adjust for sample sequencing depth, the ranking procedure was treated as a function mapping ranks to scores, and we interpolated between the observed scores to obtain scores corresponding to adjusted ranks. The ranks were adjusted in linear proportion to relative sample depth: if the relative sample depth was x, interpolated scores were taken at x*the original ranks (i.e. x=1.1, we take scores computed at ranks 1.1, 2.2, . . . , $x*2^i$). Every sample was then assigned a set of 14 adjusted extreme-rank scores to be used in further classification.

Given the feature vector, a kernel logistic regression classifier was used to capture potential non-linearities in predicting cancer/non-cancer status from the features. Specifically, a regularized kernel logistic regression classifier (KLR) was trained using the isotropic radial basis function (power exponential 2) as the kernel with scale parameter gamma, and L2 regularization parameter lambda (adjusted by dividing by $m^2$, where m is the number of samples so lambda scales naturally with the amount of training data). Gamma and lambda were optimized for holdout log-loss using internal cross-validation within specified training data, and were optimized using grid-search over the range $1,1e^{-2}$ (gamma), $1e^3$-$1e^1$ (lambda) in 7 multiplicative steps, starting at the maximum value and halving the parameter each step. The median optimal parameters over internal cross-validation folds were 0.125 for gamma and 125 for lambda.

Validation of trained cancer classifier: To evaluate performance of this extreme-rank-score classifier procedure on the CCGA substudy data set, cross-validation was applied to the training set, dividing the samples into 10 folds. Each fold was held out and the ERS classifier was trained on the remaining 9/10 of the data (using internal cross-validation within those folds to optimize gamma and lambda). The log-ratio scores used in featurization only accessed data from training folds. Output scores from each held-out fold were pooled and used to construct a Receiver-Operator Characteristic (ROC) curve for performance. For evaluating the CCGA test set, the entire training data set was used to construct scores and a single KLR classifier, which was then applied to the test data set.

Figure 9:
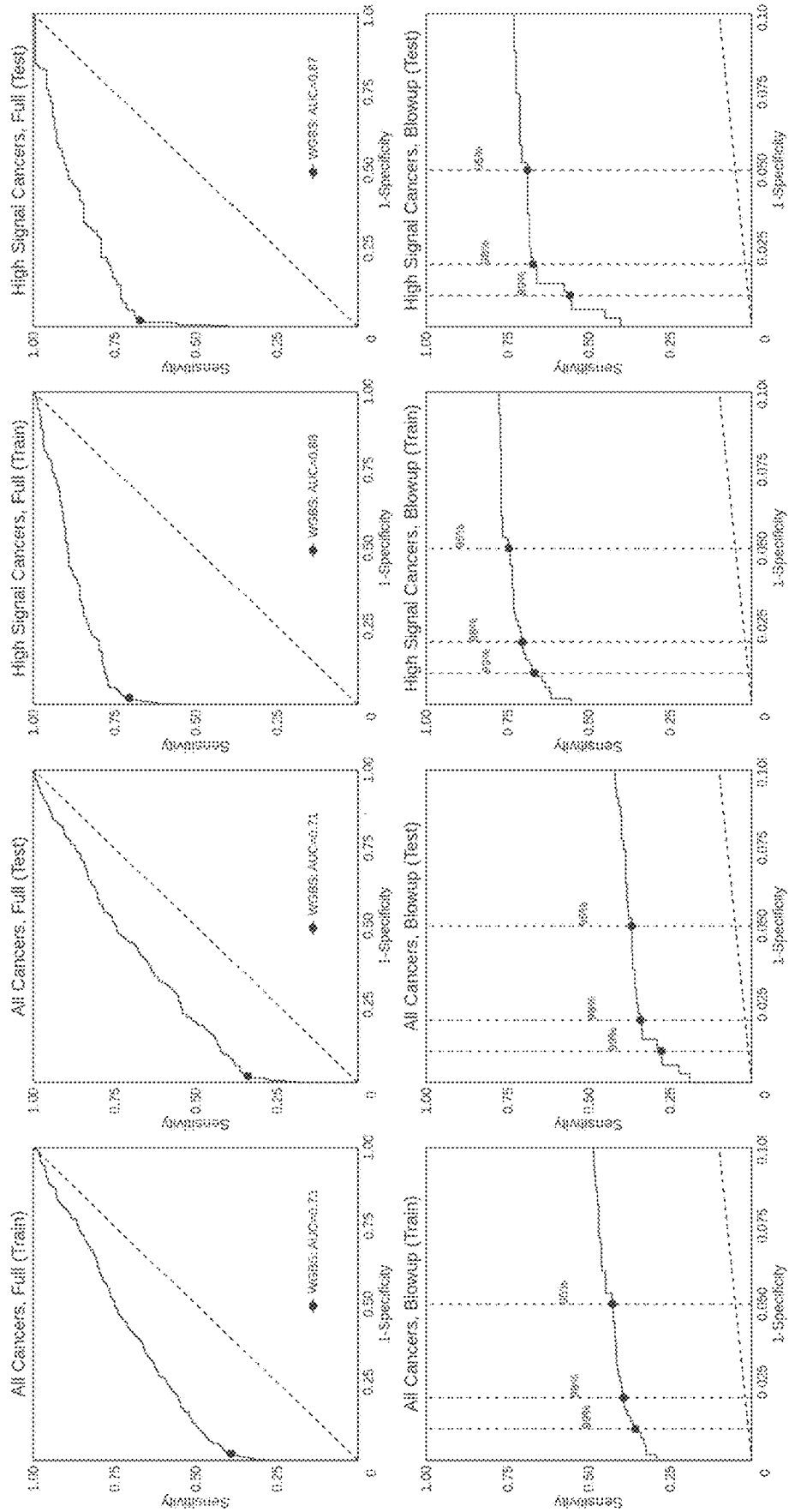
FIG. 9 provides ROC curves for all cancers (left) and high-signal cancer types (right) in the training and test sets obtained from an experiment described in VIII.A. Top panels depict the full range of specificity; bottom panels focus on 90-100% specificity to more clearly depict sensitivity at 95%, 98%, and 99% specificities, as indicated.

Sensitivity and specificity were estimated from classifiers; each classifier corrected for or suppressed assay-specific interfering biological signals (eg, CH, hematologic conditions, age-related alterations). Non-cancer cases were used to estimate specificity after correcting for interfering signal. The relationship between sensitivity and specificity is depicted by Receiver-Operator Characteristic (ROC) curves provided in FIG. 9 that demonstrated potential for high specificity with the assay. The area under the curve (AUC) values were similar in training data set and test data set. The AUC values were significant higher in a certain group of cancer (0.88 and 0.87) compared to across all cancers (0.73 and 0.71). The group of cancer, showing high specificity with the assay and referred to as "high-signal cancers" (defined as cancers with greater than 50% 5-year cancer-specific mortality) including several solid cancers (anorectal, colorectal, esophageal, head & neck, hepatobiliary, lung, ovarian, and pancreatic cancers), as well as lymphoma and multiple myeloma.

Figure 10:
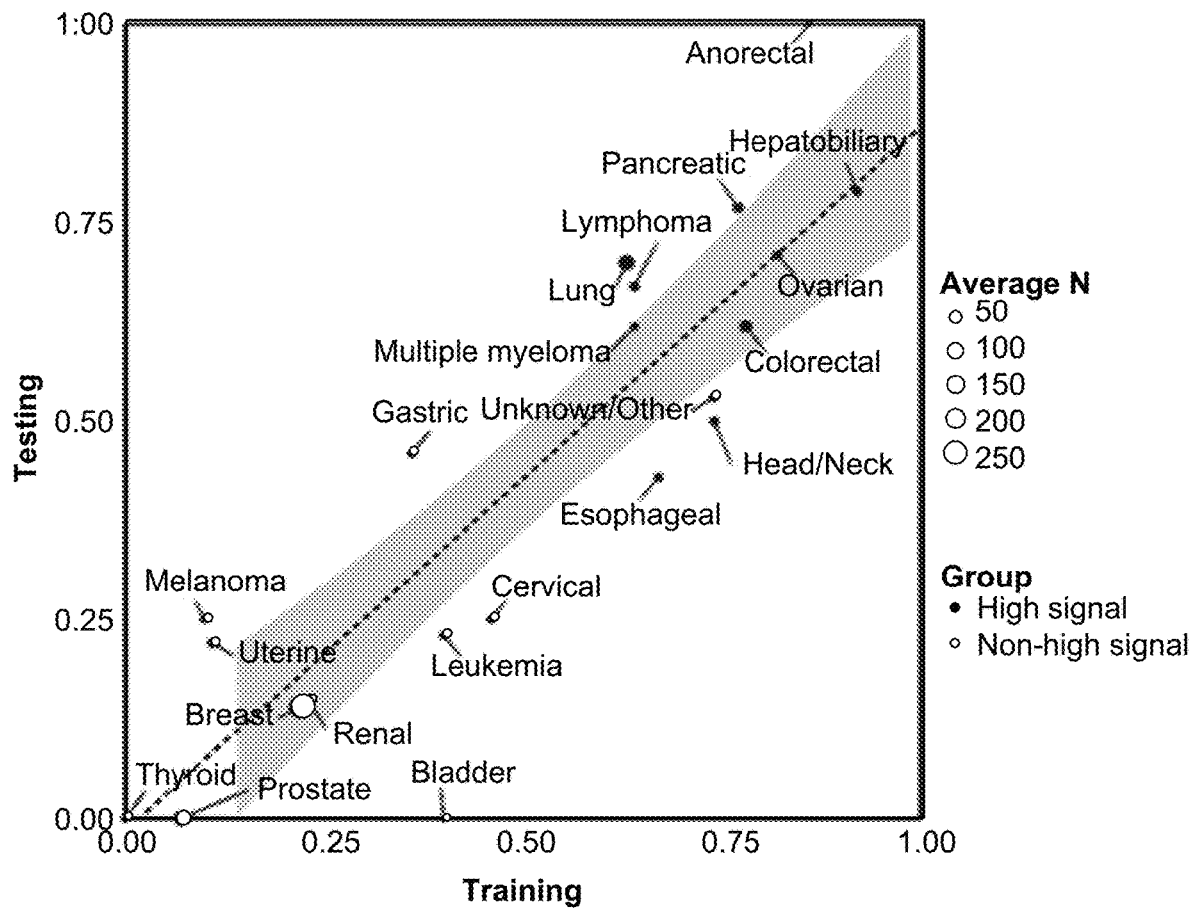
FIG. 10 shows agreement between training and test set performance. Sensitivity at 98% specificity is reported for each tumor type in training (x-axis) and test (y-axis) using the WGBS assay. High-signal cancers and sample size are indicated. Gray shading represents the 95% confidence interval of the fit line.
Figure 11A:
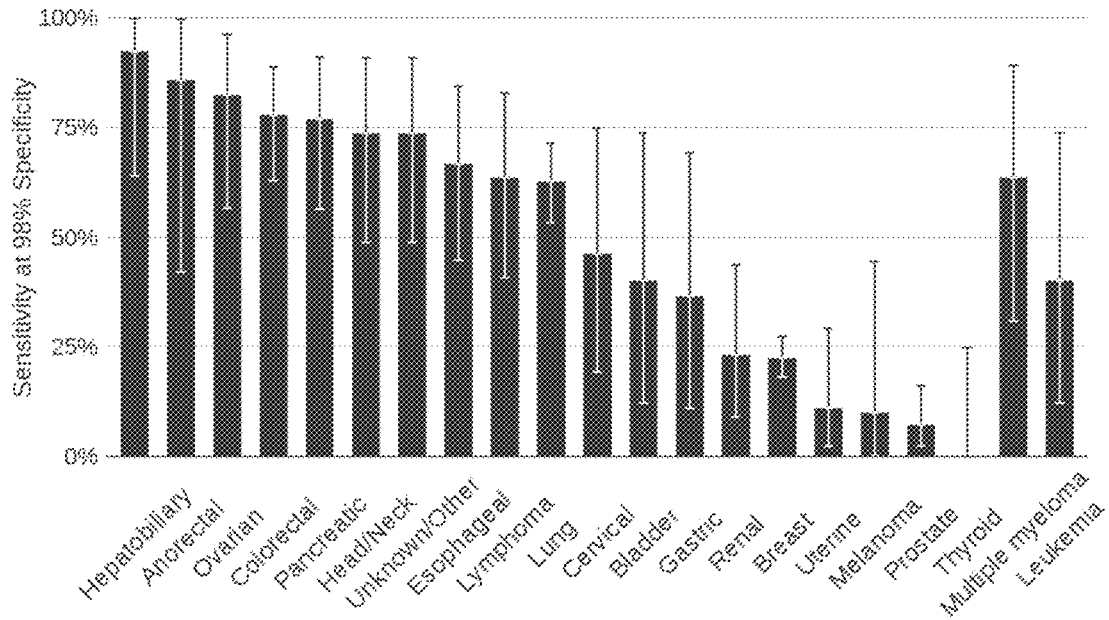
FIGS. 11A and 11B shows the sensitivity at 98% specificity (y-axis) of each tumor type (x-axis) in the training (FIG. 11A) and test sets (FIG. 11B) when analyzed by the WGBS. Error bars represent 95% confidence intervals.
Figure 11B:
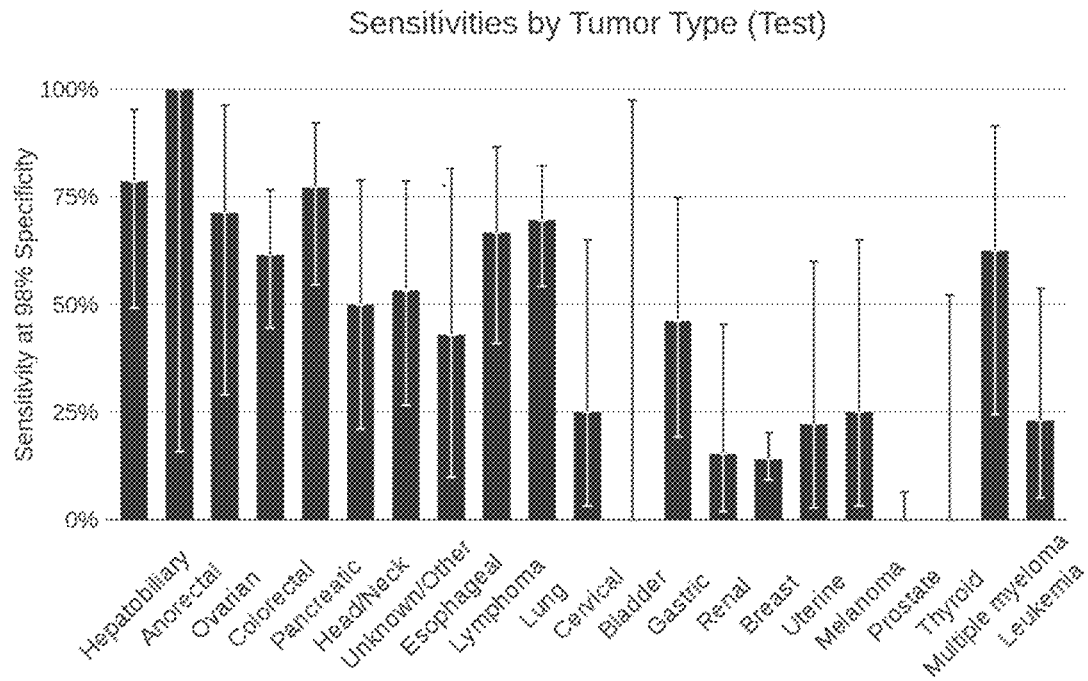

Sensitivity was further studied at a cut-off with 98% specificity to (1) allow for an estimated occult cancer rate of approximately 1.3% per year in persons aged ≥50 years (SEER), and (2) account for ongoing follow-up of the non-cancer participants. Sensitivity estimates were generally consistent between training and test sets across cancer types (FIG. 10). Results are further depicted in FIGS. 11A-B and Table 1.

TABLE 1

| Sensitivity (95% CI) | Training/ Cross-Validation | | Test | |
|---|---|---|---|---|
| | n | WGBS | n | WGBS |
| Anorectal | 7 | 86% (42-100) | 2 | 100% (16-100) |
| Bladder | 10 | 40%, (12-74) | 1 | 0% (0-98) |
| Breast | 339 | 22% (18-27) | 170 | 14% (9-20) |
| Cervical | 13 | 46% (19-75) | 8 | 25% (3-65) |
| Colorectal | 45 | 78% (63-89) | 39 | 62% (45-77) |
| Esophageal | 24 | 67% (45-84) | 7 | 43% (10-82) |
| Gastric | 11 | 36% (11-69) | 13 | 46% (1975) |
| Head & Neck | 19 | 74% (49-91) | 12 | 50% (21-79) |
| Hepatobiliary | 13 | 92% (64-100) | 14 | 79% (49-95) |
| Leukemia | 10 | 40% (12-74) | 13 | 23% (5-54) |
| Lung | 118 | 63% (53-71) | 46 | 70% (54-82) |
| Lymphoma | 22 | 64% (41-83) | 18 | 67% (41-87) |
| Melanoma | 10 | 10% (0-45) | 8 | 25% (3-65) |
| Multiple Myeloma | 11 | 64% (31-89) | 8 | 62% (24-91) |
| Ovarian | 17 | 82% (57-96) | 7 | 71% (29-96) |
| Pancreatic | 26 | 77% (56-91) | 22 | 77% (55-92) |
| Prostate | 69 | 7% (2-16) | 55 | 0% (0-6) |
| Renal | 26 | 23% (9-44) | 13 | 15% (2-45) |
| Thyroid | 13 | 0 (0-25) | 5 | 0% (0-52) |
| Uterine | 27 | 11% (2-29) | 9 | 22% (3-60) |
| Multiple Primaries | 6 | 50% (12-88) | 0 | — |
| Unknown Primary/Other | 19 | 74% (49-91) | 15 | 53% (27-79) |

CI: Confidence interval.
WGS: Whole-genome sequencing.
WGBS: Whole-genome bisulfite sequencing.
Data include stages I-IV.

Overall sensitivity at 98% specificity was 39.5% (36-43%) in the training set across all cancer types; this was consistent in the test set (34.2% [30-39%]). As expected, sensitivity increased with cancer stage. Sensitivity at 98% specificity in high-signal cancers was 70.2% (65-75%) in the training set at 98% specificity, which was consistent in the test set (66.9% [59-74%]).

The results show that cfDNA sequencing and analysis of their methylation status can detect cancer with high specificity. This supports feasibility for use in early detection, potentially detecting a larger proportion of cancers, including some high-mortality cancers, across stages.

VIII. Additional Considerations

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment, thereby providing a framework for various possibilities of described embodiments to function together.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method for detecting cancer in a test subject from a cell-free deoxyribonucleic acid (cfDNA) sample fragment, the method comprising:
   building a data structure from a set of training fragments by:
      for each training fragment in the set of training fragments, generating a training state vector comprising a known genomic location within a reference genome and a methylation state for each of a plurality of CpG sites in the training fragment, each methylation state determined to be methylated or unmethylated;
      determining a plurality of strings, wherein each string is a portion of the training state vector,
      quantifying a count of each string from the training state vectors, and
      storing a plurality of counts for each string in the data structure;
   accessing the data structure comprising the counts of the strings of the plurality of CpG sites within the reference genome and their respective methylation states from the set of training fragments;
   generating a sample state vector for a sample fragment comprising a sample genomic location within the reference genome and a methylation state for each of a plurality of CpG sites in the sample fragment, each methylation state determined to be methylated or unmethylated;
   generating a list of possibilities of a methylation state vector from the sample genomic location that are of a same length as the sample state vector, wherein each possibility of the methylation state vector is distinct from other possibilities of the methylation state vector;
   for each possibility of the methylation state vector, calculating a probability by accessing the counts stored in the data structure;
   identifying the possibility of the methylation state vector that matches the sample state vector and correspondingly the calculated probability as a sample probability;
   based on the sample probability, generating a score for the sample fragment of the sample state vector relative to the set of training fragments by:
      identifying one or more of the calculated probabilities for possibilities of the methylation state vector that are less than the sample probability, and
      generating the score for the sample fragment by summing the one or more identified calculated probabilities with the sample probability;
   determining whether the sample fragment has an anomalous methylation pattern based on the generated score; and
   in response to determining the sample fragment to have an anomalous methylation pattern, applying a cancer classifier to the sample state vector to determine a cancer prediction for the test subject that originated the sample fragment, wherein a cancer treatment is prescribed based on the cancer prediction.

2. The method of claim 1, wherein each of the strings of CpG sites comprises the methylation state for each of the CpG sites at a plurality of genomic locations within the reference genome, wherein each of the methylation states is determined to be methylated or unmethylated.

3. The method of claim 1, wherein determining whether the sample fragment has an anomalous methylation pattern based on the generated score further comprises determining whether the generated score for the sample fragment is below a threshold score, wherein the threshold score indicates a degree of confidence that the sample fragment has an anomalous methylation pattern.

4. The method of claim 1, wherein the set of training fragments comprise training fragments from one or more healthy subjects, wherein the one or more healthy subjects lack a specific medical disorder and wherein the sample fragment is determined to be anomalously methylated relative to the set of training fragments from the one or more healthy subjects.

5. The method of claim 1, wherein calculating a probability by accessing the counts stored in the data structure for each of the possibilities comprises:
   for each of a plurality of conditional elements, wherein each conditional element is a conditional probability considering a subset of CpG sites in the possibility,
   calculating a Markov chain probability of an order with the plurality of counts stored in the data structure by:
      identifying a first count of number of strings matching that conditional element;
      identifying a second count of number of strings matching that conditional element's prior methylation states up to a whole number length; and
      calculating the Markov chain probability by dividing the first count by the second count.

6. The method of claim 5, wherein calculating the Markov chain probability of the order with the plurality of counts stored in the data structure further comprises implementing a smoothing algorithm.

7. The method of claim 1, wherein the sample state vector is partitioned into a plurality of windows comprising a first window and a second window, wherein the first window and the second window are two different portions of the sample fragment; wherein identifying the possibility that matches the sample state vector and correspondingly the calculated probability as the sample probability comprises identifying a first possibility with a first sample probability that matches the first window and a second possibility with a second sample probability that matches the second window; and wherein the generated score is based on one of the first sample probability and the second sample probability.

8. The method of claim 1, further comprising filtering a plurality of sample fragments based on the generated scores for each sample fragment, resulting in a subset of sample fragments having anomalous methylation patterns.

9. The method of claim 1, further comprising:
identifying the sample fragment as hypermethylated when the sample fragment comprises at least a threshold number of CpG sites with more than a threshold percentage of the CpG sites being methylated, wherein the threshold number of CpG sites is 5 or more CpG sites, and wherein the threshold percentage of CpG sites methylated is 80% or greater; or
identifying the sample fragment as hypomethylated when the sample fragment comprises at least a threshold number of CpG sites with more than a threshold percentage of the CpG sites being unmethylated, wherein the threshold number of CpG sites is 5 or more CpG sites, and wherein the threshold percentage of CpG sites unmethylated is 80% or greater.

10. The method of claim 1, wherein the cancer classifier is trained with a cancer set of training fragments from one or more subjects with cancer and a non-cancer set of training fragments from one or more subjects without cancer.

11. The method of claim 1, wherein applying the cancer classifier to the sample state vector generates at least one of a cancer probability and a non-cancer probability, wherein the cancer prediction comprises a cancer status score based on at least one of the cancer probability and the non-cancer probability.

12. A non-transitory computer-readable storage medium storing instructions for detecting cancer in a test subject from a cell-free deoxyribonucleic acid (cfDNA) sample fragment, the instructions that, when executed by a processor, cause the processor to perform operations comprising:
building a data structure from a set of training fragments by:
for each training fragment in the set of training fragments, generating a training state vector comprising a known genomic location within a reference genome and a methylation state for each of a plurality of CpG sites in the training fragment, each methylation state determined to be methylated or unmethylated;
determining a plurality of strings, wherein each string is a portion of the training state vector,
quantifying a count of each string from the training state vectors, and
storing a plurality of counts for each string in the data structure;
accessing the data structure comprising the counts of the strings of the plurality of CpG sites within the reference genome and their respective methylation states from the set of training fragments;
generating a sample state vector for a sample fragment comprising a sample genomic location within the reference genome and a methylation state for each of a plurality of CpG sites in the sample fragment, each methylation state determined to be methylated or unmethylated;
generating a list of possibilities of a methylation state vector from the sample genomic location that are of a same length as the sample state vector, wherein each possibility of the methylation state vector is distinct from other possibilities of the methylation state vector;
for each possibility of the methylation state vector, calculating a Markov chain probability by accessing the counts stored in the data structure;
identifying the possibility of the methylation state vector that matches the sample state vector and correspondingly the calculated probability as a sample probability;
based on the sample probability, generating a score for the sample fragment of the sample state vector relative to the set of training fragments by:
identifying one or more of the calculated probabilities for possibilities of the methylation state vector that are less than the sample probability, and
generating the score for the sample fragment by summing the one or more identified calculated probabilities with the sample probability;
determining whether the sample fragment has an anomalous methylation pattern based on the generated score; and
in response to determining the sample fragment to have an anomalous methylation pattern, applying a cancer classifier to the sample state vector to determine a cancer prediction for the test subject that originated the sample fragment, wherein a cancer treatment is prescribed based on the cancer prediction.

13. The non-transitory computer-readable storage medium of claim 12, wherein each of the strings of CpG sites comprises the methylation state for each of the CpG sites at a plurality of genomic locations within the reference genome, wherein each of the methylation states is determined to be methylated or unmethylated.

14. The non-transitory computer-readable storage medium of claim 12, wherein determining whether the sample fragment has an anomalous methylation pattern based on the generated score further comprises determining whether the generated score for the sample fragment is below a threshold score, wherein the threshold score indicates a degree of confidence that the sample fragment has an anomalous methylation pattern.

15. The non-transitory computer-readable storage medium of claim 12, wherein the set of training fragments comprise training fragments from one or more healthy subjects, wherein the one or more healthy subjects lack a specific medical disorder and wherein the sample fragment is determined to be anomalously methylated relative to the set of training fragments from the one or more healthy subjects.

16. The non-transitory computer-readable storage medium of claim 12, wherein calculating a probability by accessing the counts stored in the data structure for each of the possibilities comprises:
for each of a plurality of conditional elements, wherein each conditional element is a conditional probability considering a subset of CpG sites in the possibility,
calculating a Markov chain probability of an order with the plurality of counts stored in the data structure by:
identifying a first count of number of strings matching that conditional element;
identifying a second count of number of strings matching that conditional element's prior methylation states up to a whole number length; and
calculating the Markov chain probability by dividing the first count by the second count.

17. The non-transitory computer-readable storage medium of claim 16, wherein calculating a Markov chain probability of an order with the plurality of counts stored in the data structure further comprises implementing a smoothing algorithm.

18. The non-transitory computer-readable storage medium of claim 12, wherein the sample state vector is partitioned into a plurality of windows comprising a first window and a second window, wherein the first window and the second window are two different portions of the sample fragment; wherein identifying the possibility that matches the sample state vector and correspondingly the calculated probability as the sample probability comprises identifying a first possibility with a first sample probability that matches the first window and a second possibility with a second sample probability that matches the second window; and wherein the generated score is based on one of the first sample probability and the second sample probability.

19. The non-transitory computer-readable storage medium of claim 12, the operations further comprising filtering a plurality of sample fragments based on the generated scores for each sample fragment, resulting in a subset of sample fragments having anomalous methylation patterns.

20. The non-transitory computer-readable storage medium of claim 12, the operations further comprising:
   identifying the sample fragment as hypermethylated when the sample fragment comprises at least a threshold number of CpG sites with more than a threshold percentage of the CpG sites being methylated, wherein the threshold number of CpG sites is 5 or more CpG sites, and wherein the threshold percentage of CpG sites methylated is 80% or greater; or
   identifying the sample fragment as hypomethylated when the sample fragment comprises at least a threshold number of CpG sites with more than a threshold percentage of the CpG sites being unmethylated, wherein the threshold number of CpG sites is 5 or more CpG sites, and wherein the threshold percentage of CpG sites unmethylated is 80% or greater.

21. The non-transitory computer-readable storage medium of claim 12, wherein the cancer classifier is trained with a cancer set of training fragments from one or more subjects with cancer and a non-cancer set of training fragments from one or more subjects without cancer.

22. The non-transitory computer-readable storage medium of claim 12, wherein applying the cancer classifier to the sample state vector generates at least one of a cancer probability and a non-cancer probability, wherein the cancer prediction comprises a cancer status score based on at least one of the cancer probability and the non-cancer probability.

23. A system for detecting cancer in a test subject from a cell-free deoxyribonucleic acid (cfDNA) sample fragment, the system comprising:
   a computer processor; and
   a non-transitory computer-readable storage medium storing instructions that, when executed by a processor, cause the processor to perform operations comprising:
      building a data structure from a set of training fragments by:
         for each training fragment in the set of training fragments, generating a training state vector comprising a known genomic location within a reference genome and a methylation state for each of a plurality of CpG sites in the training fragment, each methylation state determined to be methylated or unmethylated;
         determining a plurality of strings, wherein each string is a portion of the training state vector,
         quantifying a count of each string from the training state vectors, and
         storing a plurality of counts for each string in the data structure;
      accessing the data structure comprising the counts of the strings of the plurality of CpG sites within the reference genome and their respective methylation states from the set of training fragments;
      generating a sample state vector for a sample fragment comprising a sample genomic location within the reference genome and a methylation state for each of a plurality of CpG sites in the sample fragment, each methylation state determined to be methylated or unmethylated;
      generating a list of possibilities of a methylation state vector from the sample genomic location that are of a same length as the sample state vector, wherein each possibility of the methylation state vector is distinct from other possibilities of the methylation state vector;
      for each possibility of the methylation state vector, calculating a Markov chain probability by accessing the counts stored in the data structure;
      identifying the possibility of the methylation state vector that matches the sample state vector and correspondingly the calculated probability as a sample probability;
      based on the sample probability, generating a score for the sample fragment of the sample state vector relative to the set of training fragments by:
         identifying one or more of the calculated probabilities for possibilities of the methylation state vector that are less than the sample probability, and
         generating the score for the sample fragment by summing the one or more identified calculated probabilities with the sample probability;
      determining whether or not the sample fragment has an anomalous methylation pattern based on the generated score; and
      in response to determining the sample fragment to have an anomalous methylation pattern, applying a cancer classifier to the sample state vector to determine a cancer prediction for the test subject that originated the sample fragment, wherein a cancer treatment is prescribed based on the cancer prediction.

* * * * *